US006992085B2

(12) United States Patent
Goldstein et al.

(10) Patent No.: US 6,992,085 B2
(45) Date of Patent: Jan. 31, 2006

(54) OCTAHYDRO-2H-PYRIDO[1,2-A]PYRAZINE COMPOUNDS

(75) Inventors: Solo Goldstein, Suresnes (FR); Guillaume Poissonnet, Orsay (FR); Jean-Gilles Parmentier, Issy les Moulineaux (FR); Pierre Lestage, La Celle Saint Cloud (FR); Brian Lockhart, Croissy sur Seine (FR)

(73) Assignee: Les Laboratories Servier, Courbevoie Cedex (FR)

( * ) Notice: Subject to any disclaimer, the term of this patent is extended or adjusted under 35 U.S.C. 154(b) by 23 days.

(21) Appl. No.: 10/195,019

(22) Filed: Jul. 12, 2002

(65) Prior Publication Data

US 2003/0195216 A1 Oct. 16, 2003

(30) Foreign Application Priority Data

Jul. 12, 2001 (FR) .................................. 01 09260

(51) Int. Cl.
*A61K 31/4985* (2006.01)
*C07D 471/04* (2006.01)

(52) U.S. Cl. ..................................... 514/249; 544/349
(58) Field of Classification Search ............... 544/349; 514/249
See application file for complete search history.

(56) References Cited

U.S. PATENT DOCUMENTS 3,388,128 A * 6/1968 Day ........................... 544/349

FOREIGN PATENT DOCUMENTS

WO  94/06794  * 3/1994

OTHER PUBLICATIONS

Phillips et al. in Annual Reports in Medicinal Chemistry, vol. 33, p. 31-40 (1998).*
Koshinaka et al.,Chemical Abstacts, vol. 87, No. 68417 (1977), Abstract for JP 5202188 (Jan. 29, 1977).*
Horrigan, Exp.Opin. Pharmacother. vol. 2, p. 573-586 (2001).*
Arrang, et al., *European Journal of Pharmacology—Molecular Pharmacology Section*, 1990, 188, 219-227.
Philippu, et al., *Behavioural Brain Research*, 2001, 124, 151-159.
Bacciottini, et al., *Behavioural Brain Research*, 2001, 124, 183-194.
Kim, et al., *Neuroscience Letters*, 2002, 321, 169-172.
Leurs, et al., *TiPS*, May 1998, vol. 19, 177-183.
Tozer, et al.,*Exp. Opin. Ther. Patents*, 2000, 10, 1045-1055.
Passani, et al., *Neuroscience and Biobehavioral Reviews*, 2000, 24, 107-113.
Fox, et al., *Journal of Pharmacology and Experimental Therapeutics*, 2003, 305, 897-908.
Ligneau, et al., *Journal of Pharmacology and Experimental Therapeutics*, 1998, 287, 658-666.
Monti, et al., *European Journal of Pharmacology*, 1991, 205, 283-287.
Stark, et al., *Drugs of the Future*, 1996, 21, 507-520.
Howard, *Exp. Opin. Ther. Patents*, 2000, 10, 1549-1559.
Itoh, et al., *Biol. Psychiatry*, 1999, 45, 475-481.
Masaki, et al., *Diabetes*, 2001, 50, 376-384.
Masaki, et al., *Endocrinology*, 2003, 144, 2741-2748.
Rouleau, et al.,*Journal of Pharmacology and Experimental Therapeutics*, 1997, 281, 1085-1094.
A-431404, *Pharmaproject*, Preclinical Trial, 2005.

(Continued)

*Primary Examiner*—Richard L. Raymond
(74) *Attorney, Agent, or Firm*—Hueschen and Sage

(57) ABSTRACT

A compound selected from those of formula (I):

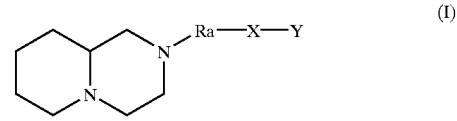

wherein:
Ra represents linear or branched $(C_1-C_6)$alkylene,
X represents a group selected from $W_1$, $—C(W_1)—W_2—$, $—W_2—C(W_1)—$, $—W_2—C(W_1)W_2—$, $—W_2—Ra—$ and $—CH(OR_1)—$ wherein $W_1$, $W_2$ and $R_1$ are as defined in the description, when Y represents aryl or heteroaryl,
or
X represents a group selected from single bond, $—C(W_1)—$, $—W_2—C(W_1)—$, $—W_2—Ra$ and $—CH(OR_1)—$ wherein $W_1$, $W_2$, Ra and $R_1$ are as defined hereinbefore, when Y represents a fused bicyclic group, of formula:

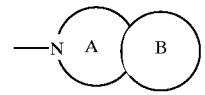

wherein:
A represents nitrogen-containing heterocycle having from 4 to 7 ring members that is unsaturated or partially saturated and optionally contains a second hetero atom,
B represents phenyl ring optionally substituted by one or more groups as defined in the description,
its isomers, and addition salts thereof with a pharmaceutically acceptable acid or base, medicinal products containing the same are useful in the treatment of cognitive deficiencies.

10 Claims, No Drawings

OTHER PUBLICATIONS

3H-A-349821, *Pharmaproject*, Preclinical Trial, 2005.
Perry, et al., *The Lancet*, 1977, 189.
Perry, et al., *British Medical Journal*, 1978, 2, 1457-1459.
Blandina, et al., *British Journal of Pharmacology*, 1996, 119, 1656-1664.
Cecchi, et al., *European Journal of Neuroscience*, 2001, 13, 68-78.
Philippu, et al., *Drug News Perspect*, 2001, 14, 523-529.
Perio, et al., *Psychopharmacology*, 1989, 97, 262-268.
Morris, et al., *Nature*, 1982, 297, 681-683.
Miyazaki, et al., *Life Sciences*, 1995, 57, 2137-2144.
Meguro, *Pharmacology Biochemistry and Behavior*, 1995, 50, 321-325.
Prast, et al., *Brain Research*, 1996, 734, 316-318.
Ghi, et al., *Prog. Neuro-Psychopharmacol & Biol. Psychiat.*, 1998, 22, 387-395.
Flood, et al., *Psychopharmacology*, 1998, 140, 279-284.

* cited by examiner

OCTAHYDRO-2H-PYRIDO[1,2-A]PYRAZINE COMPOUNDS

The present invention relates to new octahydro-2H-pyrido [1,2-a]pyrazine compounds.

1. Field of the Invention

The compounds of the present invention are especially valuable from a pharmacological point of view because of their specific interaction with type H3 central histamine receptors and can be used in the treatment of neuropathologies associated with cerebral ageing, mood disorders, eating behaviour and the pattern of wakefulness and sleep, and of attention deficit hyperactivity syndrome.

Ageing of the population due to increased life expectancy at birth has brought with it a large increase in the incidence of age-related neuropathologies and especially of Alzheimer's disease. The principal clinical manifestations of cerebral ageing and especially of age-related neuropathologies are deficiencies in mnemic and cognitive functions, which may lead to dementia.

At the level of the central nervous system, recent neuropharmacological studies have shown that histamine via the central histaminergic systems plays the role of a neurotransmitter or neuromodulator in physiological or physiopathological situations (Annu. Rev. Neurosci., 1986, 9, 209–254; Physiol. Rev., 1991, 71, 1–51). Thus, it has been shown that histamine is involved in various physiological and behavioural processes, such as thermoregulation, neuro-endocrinal regulation, the circadian rhythm, cataleptic states, motility, aggressiveness, eating behaviour, learning and memorisation, and synaptic plasticity (Hass et al., histaminergic neurones:morphology and function, Boca Roton, Fla.: CRC Press, 1991, pp. 196–208; Prog. Neurobiology, 2001, 63, 637–672).

Of the 3 histamine receptor sub-types (H1, H2 and H3), it was initially shown that the type H3 receptor is a pre-synaptic autoreceptor which controls the release of histamine (Nature, 1987, 327, 117–123). Its activation inhibits the release and synthesis of histamine by a negative feedback mechanism (Neuroscience, 1987, 23, 149–157). The existence of presynaptic heteroreceptors capable of modulating the release of some neuropeptides and of many neurotransmitters, such as noradrenaline, serotonin, dopamine, GABA, acetylcholine and glutamate (TiPS, 1998, 19, 177–183) was then demonstrated. Studies carried out on animals have shown that an increase in endogenous extra-synaptic levels of histamine via blockage of the type H3 receptors by H3 antagonists makes it possible to promote states of vigilence, learning and memory processes, to regulate food intake, and combat convulsive attacks (Prog. Neurobiol., 2000, 63, 637–672; Neurosci. Biobehav. Rev., 2000, 24, 107–113). As a result, the potential therapeutic indications for H3 antagonists are the treatment of cognitive deficiencies associated with cerebral ageing and with neurodegenerative diseases such as Alzheimer's disease, Parkinson's disease, Pick's disease, Korsakoffs disease and frontal or sub-cortical dementia of vascular or other origin, and the treatment of mood disorders, convulsive attacks, attention deficit hyperactivity syndrome, obesity and pain.

2. Description of the Prior Art

Several patent applications or Patent Specifications, such as JP 52012188, WO 94/06794 and U.S. Pat. No. 3,388,128 describe compounds containing an octahydro-2H-pyrido[1, 2-a]pyrazine structure. Such compounds are claimed for their vasodilatory activity or for their use in the treatment of hypotension, cerebral ischaemia, psychoses or convulsions. None of those documents describes or suggests for those compounds an H3 central histamine receptor antagonist activity, which is the novel property of the compounds claimed by the Applicant.

DETAILED DESCRIPTION OF THE INVENTION

More especially, the present invention relates to compounds of formula (I):

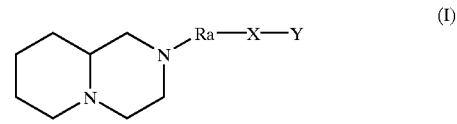

(I)

wherein:
Ra represents a linear or branched ($C_1$–$C_6$)alkylene chain,
X represents a group selected from $W_1$, —C($W_1$)—$W_2$—, —$W_2$—C($W_1$)—, —$W_2$—C($W_1$)$W_2$—, —$W_2$—Ra— wherein Ra is as defined hereinbefore, and —CH(OR$_1$)— wherein:
  $W_1$ represents an oxygen atom, a sulphur atom or a group of formula —NR$_2$ wherein R$_2$ represents a group selected from a hydrogen atom, linear or branched ($C_1$–$C_6$)alkyl, aryl, aryl-($C_1$–$C_6$)alkyl in which the alkyl moiety is linear or branched, and linear or branched ($C_1$–$C_6$)acyl,
  $W_2$ represents a group as defined for $W_1$,
  $R_1$ represents a group selected from a hydrogen atom and a linear or branched ($C_1$–$C_6$)alkyl group,
when Y represents an aryl or heteroaryl group, or X represents a group selected from a single bond, —C($W_1$)—, —$W_2$—C($W_1$)—, —$W_2$—Ra— and —CH(OR$_1$)— wherein $W_1$, $W_2$, Ra and $R_1$ are as defined hereinbefore,
when Y represents a fused bicyclic group, of formula:

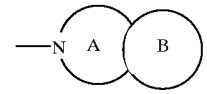

wherein:
A represents a nitrogen-containing heterocycle containing from 4 to 7 ring members that is unsaturated or partially saturated and optionally contains a second hetero atom selected from oxygen, nitrogen and sulphur, and is optionally substituted by one or more groups selected from oxo and linear or branched ($C_1$–$C_6$)alkyl,
B represents a phenyl ring optionally substituted by one or more groups selected from halogen atoms and the groups nitro, cyano, hydroxy, linear or branched ($C_1$–$C_6$)alkoxy, linear or branched ($C_1$–$C_6$)alkyl, linear or branched trihalo-($C_1$–$C_6$)alkyl, linear or branched ($C_1$–$C_6$)acyl, linear or branched ($C_1$–$C_6$)acyloxy, carboxy, linear or branched ($C_1$–$C_6$)alkoxy-carbonyl, —SH, linear or branched ($C_1$–$C_6$)-alkylsuiphanyl, and amino optionally substituted by one or two identical or different groups selected from linear or branched ($_1$–C$_6$)alkyl, aryl and aryl-($_1$–C$_6$)alkyl in which the alkyl moiety is linear or branched, their enantiomers, diastercoisomers, and addition salts thereof with a pharmaceutically acceptable acid or base, with the proviso that the compounds:

2-octahydro-2H-pyrido[1,2-a]pyrazin-2-yl-1-phenylethanol, 3-octahydro-2H-pyrido[1,2-a]pyrazin-2-ylpropyl-3,4,5-trimethoxybenzoate, and 2-octahydro-2H-pyrido[1,2-a]pyrazin-2-ylethyl-3,4,5-trimethoxybenzoate, are not included in the compounds of the invention.

"Aryl group" is understood to mean a monocyclic or bicyclic aromatic system, containing from 5 to 10 carbon atoms, optionally substituted by one or more identical or different groups each independently of the others selected from halogen atoms and the groups nitro, cyano, hydroxy, linear or branched (C$_1$–C$_6$)alkoxy, aryloxy, aryl-(C$_1$–C$_6$)alkoxy in which the alkoxy moiety is linear or branched, linear or branched (C$_1$–C$_6$)alkyl, linear or branched (C$_2$–C$_6$)alkenyl, linear or branched (C$_2$–C$_6$)alkynyl, linear or branched trihalo-(C$_1$–C$_6$)alkyl, carboxy, linear or branched (C$_1$–C$_6$)alkoxy-carbonyl, linear or branched (C$_1$–C$_6$)acyl, linear or branched (C$_1$–C$_6$)acyloxy, —SH, linear or branched (C$_1$–C$_6$)alkylsulphanyl, methylenedioxy, ethylenedioxy, —C(CH$_3$)=N—OH, and amino optionally substituted by one or two identical or different groups each independently of the other selected from linear or branched (C$_1$–C$_6$)alkyl, aryl, aryl-(C$_1$–C$_6$)alkyl in which the alkyl moiety is linear or branched, and linear or branched (C$_1$–C$_6$) acyl.

"Heteroaryl group" is understood to mean a monocyclic or bicyclic aromatic system, containing from 5 to 10 ring members, and containing within the cyclic system from 1 to 3 identical or different hetero atoms each independently of the others selected from an oxygen atom, a nitrogen atom and a sulphur atom, each of the said systems being optionally substituted by one or more identical or different groups each independently of the others selected from the list of substituents described above in the case of an aryl group.

"Isomer" is understood to include the optical isomers, enantiomers and diastereoisomers.

Among the aryl groups there may be mentioned, by way of example, the groups phenyl, naphthyl and benzocyclobutyl.

Among the heteroaryl groups there may be mentioned by way of example the groups furyl, thienyl, pyrrolyl, pyrazolyl, imidazolyl, oxazolyl, pyridyl, pyrimidinyl, pyrazinyl, benzothienyl, benzofuryl, indolyl, quinolyl, isoquinolyl, etc.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases there may be mentioned by way of non-limiting example sodium hydroxide, potassium hydroxide, triethylamine, tert-butylamine, etc.

The preferred compounds of the invention are compounds of formula (I) wherein Ra represents a linear (C$_2$–C$_5$) alkylene chain.

The R$_2$ substituents preferred according to the invention are the hydrogen atom, the linear or branched (C$_1$–C$_6$)alkyl group and the linear or branched (C$_1$–C$_6$)acyl group.

According to an advantageous variant of the invention, the preferred compounds are the compounds of formula (IA):

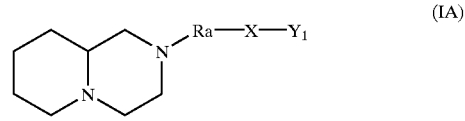

(IA)

wherein:

Ra represents a linear or branched (C$_1$–C$_6$)alkylene chain,

X represents a group selected from W$_1$, —C(W$_1$)—W$_2$—, —W$_2$—C(W$_1$)—, —W$_2$—C(W$_1$)W$_2$—, —W$_2$—Ra— wherein Ra is as defined hereinbefore, and —CH(OR$_1$)— wherein:

W$_1$ represents an oxygen atom, a sulphur atom or a group of formula —NR$_2$ wherein R$_2$ represents a group selected from a hydrogen atom, linear or branched (C$_1$–C$_6$)alkyl, aryl, aryl-(C$_1$–C$_6$)alkyl in which the alkyl moiety is linear or branched, and linear or branched (C$_1$–C$_6$)acyl, W$_2$ represents a group as defined for W$_1$, R$_1$ represents a group selected from a hydrogen atom and a linear or branched (C$_1$–C$_6$)alkyl group, Y$_1$ represents an aryl or heteroaryl group.

The X substituents preferred according to the invention in the compounds of formula (IA) are the groups selected from an oxygen atom and the groups —C(W$_1$)—W$_2$—, —W$_2$—C(W$_1$) and —N(R$_2$)— wherein W$_1$ represents an oxygen atom, W$_2$ represents an oxygen atom or an —NR$_2$ group, R$_2$ being as defined for formula (IA).

The Y$_1$ substituent preferred according to the invention is the phenyl group optionally substituted by from 1 to 3 groups selected from halogen, cyano, hydroxy, linear or branched (C$_1$–C$_6$)alkoxy, aryloxy, aryl-(C$_1$–C$_6$)alkoxy in which the alkoxy moiety is linear or branched, linear or branched (C$_1$–C$_6$)alkyl, linear or branched trihalo-(C$_1$–C$_6$) alkyl, methylenedioxy and ethylenedioxy.

According to a second advantageous variant of the invention, the preferred compounds are the compounds of formula (IB):

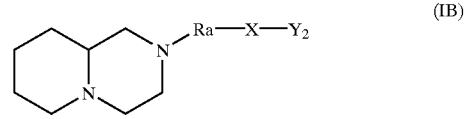

(IB)

wherein:

Ra represents a linear or branched (C$_1$–C$_6$)alkylene chain,

X represents a group selected from a single bond, —C(W$_1$)—, —W$_2$—C(W$_1$)—, —W$_2$—Ra— and —CH(OR$_1$)— wherein W$_1$, W$_2$, Ra and R$_1$ are as defined for formula (I), $Y_2$ represents a group of formula:

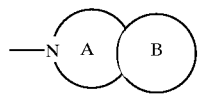

wherein A and B are as defined for formula (I).

The preferred $Y_2$ groups are the groups of formula:

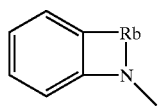

wherein Rb represents a saturated or unsaturated linear chain, containing 2 or 3 atoms selected from carbon, nitrogen and oxygen, and/or optionally containing a carbonyl group.

More especially, the $Y_2$ groups preferred according to the invention are the groups 2,3-dihydro-1H-indol-1-yl, 1H-indol-1-yl, 1H-indazol-1-yl, 1H-benzimidazol-1-yl, 3,4-dihydro-2H-quinol-1-yl, 2,3-dihydro-1H-4-quinolon-1-yl, 3,4-dihydro-2H-quinoxalin-1-yl and 2,3-dihydro-4H-1,4-benzoxazin-4-yl.

The X substituent preferred according to the invention in the compounds of formula (IB) is the meaning "single bond".

Enantiomer α and enantiomer β is understood to mean the optical isomers corresponding to the racemic mixture.

The preferred compounds of the invention are:
2-[4-(2,3-dihydro-1H-indol-1-yl)butyl]octahydro-2H-pyrido[1,2-a]pyrazine,
2-[4-(3,4,5-trimethoxyphenoxy)butyl]octahydro-2H-pyrido[1,2-a]pyrazine,
2-[4-(3,4,5-trimethoxyphenoxy)butyl]octahydro-2H-pyrido[1,2-a]pyrazine, enantiomer α,
2-[4-(3,4,5-trimethoxyphenoxy)butyl]octahydro-2H-pyrido[1,2-a]pyrazine, enantiomer β,
N-(4-octahydro-2H-pyrido[1,2-a]pyrazin-2-ylbutyl)-N-(3,4,5-trimethoxyphenyl)amine,
N-(4-octahydro-2H-pyrido[1,2-a]pyrazin-2-ylbutyl)-N-(3,4,5-trimethoxyphenyl)-amine, enantiomer α,
N-(4-octahydro-2H-pyrido[1,2-a]pyrazin-2-ylbutyl)-N-(3,4,5-trimethoxyphenyl)-amine, enantiomer β,
N-(4-trifluorophenyl)-N-(4-octahydro-2H-pyrido[1,2-a]pyrazin-2-ylbutyl)amine trihydrochloride,
N-(3,4-dichloro-phenyl)-N-(4-octahydro-2H-pyrido[1,2-a]pyrazin-2-ylbutyl)amine,
N-(3,5-dichloro-phenyl)-N-(4-octahydro-2H-pyrido[1,2-a]pyrazin-2-ylbutyl)amine,
N-(2-chlorophenyl)-N-(4-octahydro-2H-pyrido[1,2-a]pyrazin-2-ylbutyl)amine,
2-[4-(3,4-dihydro-1(2H)-quinolyl)butyl]octahydro-2H-pyrido[1,2-a]pyrazine,
2-[4-(1H-benzimidazol-1-yl)butyl]octahydro-2H-pyrido[1,2-a]pyrazine,
2-[4-(1H-indol-1-yl)butyl]octahydro-2H-pyrido[1,2-a]pyrazine,
2-[4-(1H-indazol-1-yl)butyl]octahydro-2H-pyrido[1,2-a]pyrazine,
2-[4-(2,3-dihydro-1H-indol-1-yl)butyl]octahydro-2H-pyrido[1,2-a]pyrazine, enantiomer α,
2-[4-(2,3-dihydro-1H-indol-1-yl)butyl]octahydro-2H-pyrido[1,2-a]pyrazine, enantiomer β,
3-(4-octahydro-2H-pyrido[1,2-a]pyrazin-2-ylbutoxy)benzonitrile,
3-methoxy-4-(4-octahydro-2H-pyrido[1,2-a]pyrazin-2-ylbutoxy)benzonitrile,
2-[4-(2,3,4-trimethoxyphenoxy)butyl]octahydro-2H-pyrido[1,2-a]pyrazine.

Preferably, the preferred compounds of the invention are:
4-[(4-octahydro-2H-pyrido[1,2-a]pyrazin-2-ylbutyl)amino]benzonitrile,
4-[(3-octahydro-2H-pyrido[1,2-a]pyrazin-2-ylpropoxy)benzonitrile,
4-[(3-octahydro-2H-pyrido[1,2-a]pyrazin-2-ylpropoxy)benzonitrile, enantiomer α,
4-[(3-octahydro-2H-pyrido[1,2-a]pyrazin-2-ylpropoxy)benzonitrile, enantiomer β,
4-(4-octahydro-2H-pyrido[1,2-a]pyrazin-2-ylbutoxy)benzonitrile,
4-(4-octahydro-2H-pyrido[1,2-a]pyrazin-2-ylbutoxy)benzonitrile, enantiomer α,
4-(4-octahydro-2H-pyrido[1,2-a]pyrazin-2-ylbutoxy)benzonitrile, enantiomer β,
4-(2-octahydro-2H-pyrido[1,2-a]pyrazin-2-ylethoxy)benzonitrile.

The enantiomers, diastereoisomers, and addition salts with a pharmaceutically acceptable acid or base of the preferred compounds form an integral part of the invention.

The present invention relates also to a process for the preparation of compounds of formula (I), characterised in that there is used as starting material a compound of formula (II):

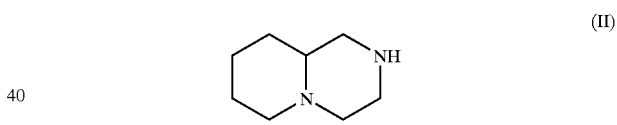

which compound of formula (II) is reacted, under basic conditions:
with a compound of formula (III):

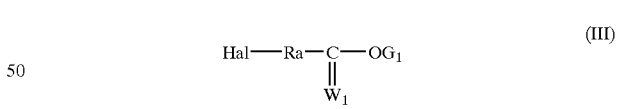

wherein Hal represents a halogen atom, Ra is as defined for formula (I) and $G_1$ represents a linear or branched ($C_1$–$C_6$) alkyl group, to yield compounds of formula (IV):

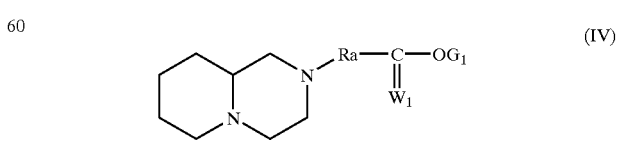

wherein Ra and $G_1$ are as defined hereinbefore, which compounds of formula (IV) are hydrolysed and then reacted, in the presence of 1-(3-dimethylaminopropyl)-3-ethylcarbodiimide hydrochloride and a tertiary amine, with a compound of formula (V):

(V)

wherein $Y_1$ represents an aryl or heteroaryl group, and $W_2$ is as defined for formula (I), to yield compounds of formula (I/a), a particular case of the compounds of formula (I):

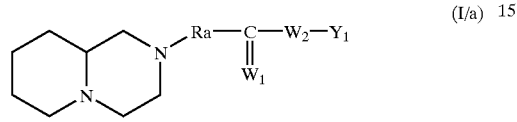
(I/a)

wherein Ra, $W_1$, $W_2$ and $Y_1$ are as defined hereinbefore, atom and Ra has the specific meaning R'a and represents a linear or branched ($C_1$–$C_5$)alkylene chain, may be reduced selectively by the action of a conventional reducing agent used in organic synthesis, to yield compounds of formula (I/b), a particular case of the compounds of formula (I):

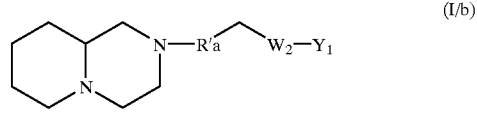
(I/b)

wherein R'a represents a linear or branched ($C_1$–$C_5$)alkylene chain, $W_2$ and $Y_1$ are as defined hereinbefore, or with a compound of formula (VI):

(VI)

wherein Hal represents a halogen atom, and $Ra_1$ represents a linear or branched ($C_1$–$C_5$)alkyl group or a bond, to yield compounds of formula (VII):

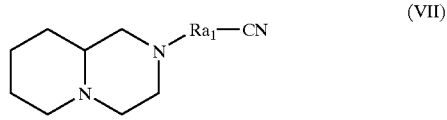
(VII)

wherein $Ra_1$ is as defined hereinbefore, the cyano function of which compounds of formula (VII) is reduced in accordance with conventional conditions to a primary amine, which compounds are then treated:

in ethanol, with a compound of formula (VIII):

(VIII)

wherein $Y_1$ is as defined hereinbefore and $W_3$ represents an oxygen or sulphur atom, to yield compounds of formula (I/c), a particular case of the compounds of formula (I):

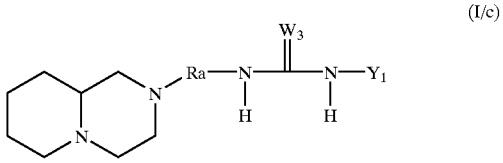
(I/c)

wherein Ra, $Y_1$ and $W_3$ are as defined hereinbefore, or, under coupling conditions, with a compound of formula (IX):

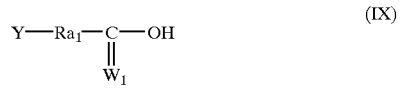
(IX)

wherein Y and $W_1$ are as defined for formula (I) and $Ra_1$ is as defined hereinbefore, to yield:

in the case when $Ra_1$ represents a bond, compounds of formula (I/d), a particular case of the compounds of formula (I):

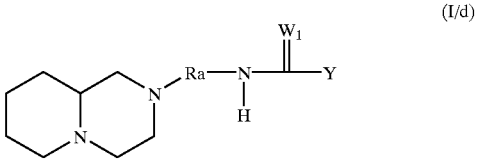
(I/d)

wherein Ra, $W_1$ and Y are as defined hereinbefore, which compounds of formula (I/d) are treated in the presence of sodium hydride with a compound of formula (X):

(X)

wherein Hal represents a halogen atom and $R'_2$ is as defined for $R_2$ in formula (I) with the exception of the definition of a hydrogen atom, to yield compounds of formula (I/e), a particular case of the compounds of formula (I):

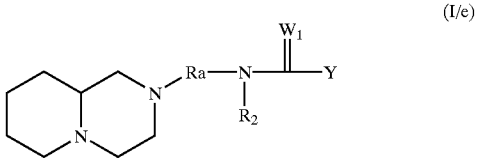
(I/e)

wherein Ra, $R_2$, $W_1$ and Y are as defined hereinbefore, or in the case when $Ra_1$ represents a linear or branched ($C_1$–$C_5$)alkylene chain, compounds of formula (XI):

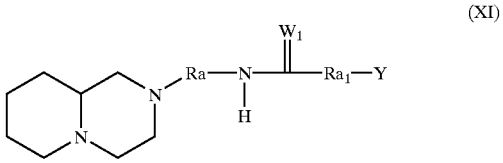
(XI)

which compounds of formula (XI) are treated with a reducing agent conventionally used in organic synthesis, to yield compounds of formula (I/f), a particular case of the compounds of formula (I):

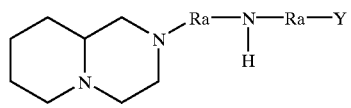
(I/f)

wherein Ra and Y are as defined for formula (I), which compounds of formula (I/f) may be subjected to the action of a compound of formula (X) as described hereinbefore, to yield compounds of formula (I/g), a particular case of the compounds of formula (I):

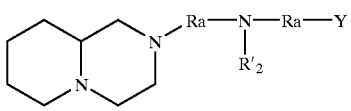
(I/g)

wherein Ra, R'$_2$ and Y are as defined hereinbefore,
or with a compound of formula (XII):

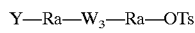
(XII)

wherein Y and Ra are as defined for formula (I) and W$_3$ represents an oxygen or sulphur atom, to yield compounds of formula (I/h), a particular case of the compounds of formula (I):

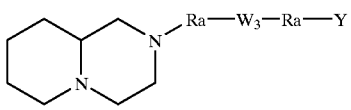
(I/h)

wherein Ra, Y and W$_3$ are as defined hereinbefore,
or with a compound of formula (XIII):

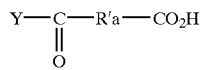
(XIII)

wherein Y and R'a are as defined for formula (I),
to yield compounds of formula (XIV):

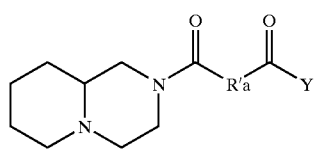
(XIV)

wherein R'a and Y are as defined hereinbefore, which compounds of formula (XIV) are treated with a reducing agent to yield compounds of formula (I/i), a particular case of the compounds of formula (I):

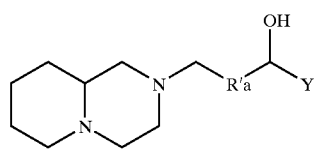
(I/i)

wherein R'a and Y are as defined for formula (I), which compounds of formula (I/i), in the case when Y represents specifically a Y$_2$ group as defined hereinbefore, are oxidised in the presence of dimethyl sulphoxide, triethylamine and oxalyl chloride, to yield compounds of formula (I/j), a particular case of the compounds of formula (I):

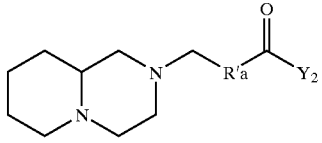
(I/j)

wherein R'a and Y$_2$ are as defined hereinbefore, or which compound of formula (I/i) is reacted with a compound of formula (XV):

(XV)

wherein Hal represents a halogen atom and R'$_1$ has the same meanings as R$_1$ with the exception of the definition of a hydrogen atom, to yield compounds of formula (I/k), a particular case of the compounds of formula (I):

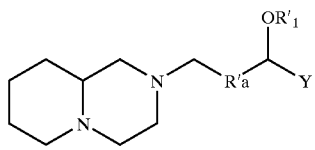
(I/k)

wherein R'a, R'$_1$ and Y are as defined hereinbefore,
or with a compound of formula (XVI):

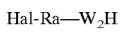
(XVI)

wherein Hal represents a halogen atom, Ra and W$_2$ are as defined for formula (I), to yield compounds of formula (XVII):

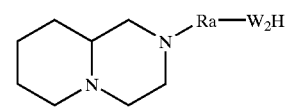
(XVII)

wherein Ra and W$_2$ are as defined hereinbefore, which compounds of formula (XVII) are treated with a compound of formula (XVIII):

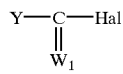
(XVIII)

wherein Hal represents a halogen atom, Y and $W_1$ are as defined for formula (I):

to yield compounds of formula (I/l), a particular case of the compounds of formula (I):

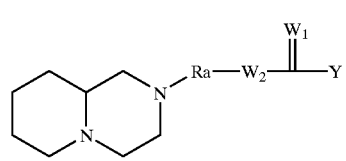
(I/l)

wherein Ra, $W_2$, $W_1$ and Y are as defined hereinbefore, which compounds of formulae (I/a) to (I/l) constitute the totality of the compounds of the invention, are purified, if necessary, in accordance with conventional purification techniques, are separated, where appropriate, into their isomers in accordance with a conventional separation technique, and are converted, if desired, into addition salts thereof with a pharmaceutically acceptable acid or base.

According to a variant of the invention, the compounds of formula (I/b), in the case when $W_2$ has the particular meaning of an oxygen or sulphur atom,

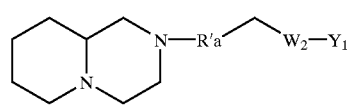
(I/b)

can be prepared starting from a compound of formula (II):

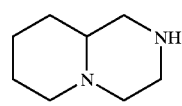
(II)

which is reacted with a compound of formula (B1):

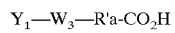
(B1)

wherein $Y_1$ represents an aryl or heteroaryl group, $W_3$ represents an oxygen or sulphur atom, R'a represents a linear or branched ($C_1$-$C_5$)alkylene chain, to yield compounds of formula ($B_2$):

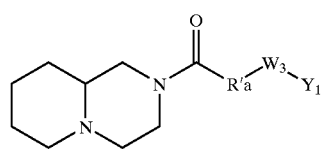
($B_2$)

wherein $Y_1$, $W_3$ and R'a are as defined hereinbefore, which compounds of formula ($B_2$) are treated with a reducing agent that is in current use in organic synthesis to yield compounds of formula (I/$b_1$), a particular case of the compounds of formula (I):

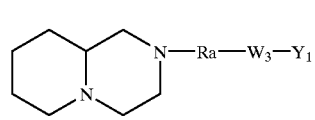
(I/$b_1$)

wherein Ra represents a linear or branched ($C_1$-$C_6$)alkylene chain, $W_3$ and $Y_1$ are as defined hereinbefore.

The compounds of formula (XII) are either commercial compounds or are obtained starting from compounds of formula (A1):

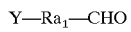
(A1)

wherein Y and $Ra_1$ are as defined for formula (I), which compounds of formula (A1) are reacted with a compound of formula (A2):

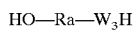
(A2)

wherein Ra and $W_3$ are as defined hereinbefore, to yield compounds of formula (A3):

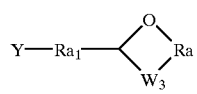
(A3)

wherein Y, $W_3$, Ra and $Ra_1$ are as defined hereinbefore, which compounds of formula (A3) are treated with DIBAL to yield compounds of formula (A4):

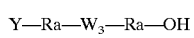
(A4)

wherein Y, Ra and $W_3$ are as defined hereinbefore, which compounds of formula (A4) are treated with tosyl chloride in a basic medium to yield compounds of formula (XII) as defined hereinbefore.

The compounds of formulae (II), (III), (V), (VI), (VII), (VIII), (IX), (X), (XII), (XIII), (XV), (XVI) and (XVIII) are either commercial products or are obtained according to conventional methods of organic synthesis.

Generally, isomers of the compounds of the invention are understood to include the optical isomers, such as the enantiomers and diastereoisomers. More especially, the pure enantiomeric forms of the compounds of the invention can be separated from the mixtures of enantiomers which are reacted with an agent capable of bringing about resolution of the racemic mixtures, said agent existing in the form of a pure enantiomer, which makes it possible to obtain the corresponding diastereoisomers. Those diastereoisomers are then separated according to separation techniques well known to the person skilled in the art, such as crystallisation or chromatography, and then the resolving agent is removed using conventional organic chemistry techniques, to yield a pure enantiomer. By another method, the pure enantiomeric forms of the compounds of the invention can be separated by chromatography on a chiral column.

The compounds of the invention that are present in the form of a mixture of diastereoisomers are isolated in pure form using conventional separation techniques, such as chromatographic techniques.

In some particular cases, the process for the preparation of the compounds of the invention can result in the predominant formation of one enantiomer or of one diastereoisomer over the other.

By virtue of their pharmacological properties as $H_3$ histamine receptor ligands, the compounds of the present invention are useful in the treatment of cognitive deficiencies associated with cerebral ageing and with neurodegenerative diseases, such as Alzheimer's disease, Parkinson's disease, Pick's disease, Korsakoffs disease and frontal or sub-cortical dementia of vascular or other origin, and in the treatment of mood disorders, convulsive attacks, attention deficit hyperactivity syndrome, obesity and pain.

The present invention relates also to pharmaceutical compositions comprising as active ingredient at least one compound of formula (I), an isomer thereof or an addition salt thereof with a pharmaceutically acceptable acid or base, alone or in combination with one or more inert, non-toxic, pharmaceutically acceptable excipients or carriers.

Among the pharmaceutical compositions according to the invention, there may be mentioned more especially those that are suitable for oral, parenteral (intravenous, intramuscular or subcutaneous), per- or trans-cutaneous, intravaginal, rectal, nasal, perlingual, buccal, ocular or respiratory administration.

The pharmaceutical compositions according to the invention for parenteral injections comprise, for example, aqueous and non-aqueous sterile solutions, dispersions, suspensions or emulsions as well as the sterile powders for the reconstitution of the injectable solutions or dispersions.

The pharmaceutical compositions according to the invention for solid oral administration include, for example, tablets or dragees, sublingual tablets, sachets, gelatin capsules, and granules, and for liquid oral, nasal, buccal or ocular administration include, for example, emulsions, solutions, suspensions, drops, syrups and aerosols.

The pharmaceutical compositions for rectal or vaginal administration are preferably suppositories, and those for per- or trans-cutaneous administration include, for example, powders, aerosols, creams, ointments, gels and patches.

The above-mentioned pharmaceutical compositions illustrate the invention but do not limit it in any way.

Among the inert, non-toxic, pharmaceutically acceptable excipients or carriers there may be mentioned by way of non-limiting example, diluents, solvents, preservatives, wetting agents, emulsifiers, dispersants, binders, swelling agents, disintegrators, retardants, lubricants, absorbency agents, suspension agents, colourants, flavourings, etc.

The useful dosage varies according to the age and weight of the patient, the route of administration, the pharmaceutical composition used, the nature and severity of the disorder, and whether any associated treatments are being taken. The dosage ranges from 10 mg to 1000 mg per day in one or more administrations.

The following Examples illustrate the invention but do not limit it in any way.

The starting materials used are known products or are prepared according to known procedures. The various Preparations yield synthesis intermediates for use in the preparation of the compounds of the invention.

The structures of the compounds described in the Examples and in the Preparations were determined in accordance with the usual spectrophotometric techniques (infrared, nuclear magnetic resonance, mass spectrometry, etc.).

The melting points were determined using either a Kofler hot plate or a hot plate under a microscope. When the compound exists in the form of a salt, the melting point given and the corresponding elemental microanalysis correspond to that of the salt product.

EXAMPLE 1

2-[4-(3,4,5-Trimethoxyphenoxy)butyl]octahydro-2H-pyrido[1,2-a]pyrazine dihydrochloride Step A: Ethyl 4-(3,4,5-trimethoxyphenoxy)butanoate 9.2 g of trimethoxyphenol, 14 g of potassium carbonate and 10.7 g of ethyl 4-bromobutanoate in 150 ml of 2-butanone are refluxed for 24 hours. The mineral salts are then filtered off and the solvent is distilled off under reduced pressure, enabling the expected compound to be obtained.

Step B: 4-(3,4,5-Trimethoxyphenoxy)butanoic acid 7 g of the compound obtained in Step A are stirred at room temperature for 72 hours in a mixture of 100 ml of ethanol and 100 ml of 1M aqueous sodium hydroxide solution. Having been rendered acidic by 100 ml of 1M hydrochloric acid, the reaction mixture is extracted with dichloromethane. The organic fractions are dried over sodium sulphate and evaporated under reduced pressure, enabling the expected product to be isolated.

Melting point: 58–60° C.

| Elemental microanalysis: | | |
|---|---|---|
| | C | H |
| % calculated | 57.77 | 6.71 |
| % found | 57.95 | 6.72 |

Step C: 1-[Octahydro-2H-pyrido[1,2-a]pyrazin-2-yl)-4-(3,4,5-trimethoxy-phenoxy-butan-1-one 3.5 g of the compound obtained in Step B, 4.5 g of 2-(1H-benzotriazol-1-yl)- 1,1,3,3-tetramethyluronium tetrafluoroborate, 2.6 ml of diisopropylethylamine and 1.96 g of octahydro-2H-pyrido[1,2-a]pyrazine in 150 ml of tetrahydrofuran are stirred for 24 hours at room temperature. The solvent is then removed under reduced pressure and the residue is taken up in a mixture of water/dichloromethane. The organic phase is dried over sodium sulphate, evaporated under reduced pressure and purified over a silica chromatography column eluted with a mixture of dichloromethane/methanol (98/2) to yield the expected product.

Step D: 2-[4-(3,4,5-Trimethoxyphenoxy)butyl]octahydro-2H-pyrido[1,2-a]pyrazine dihydrochloride 0.5 g of LiAlH$_4$ is added to 4.2 g of the compound obtained in Step C in solution in 100 ml of tetrahydrofuran, and the mixture is then stirred for 3 hours; after hydrolysis with sodium sulphate, the mineral salts are filtered off and the solvent is removed by evaporation in vacuo. The hydrochloride of the expected product is then prepared in 50 ml of ethanol using ethereal hydrogen chloride.

Melting point: 245–246° C.

| Elemental microanalysis: | | | | |
|---|---|---|---|---|
| | C | H | N | Cl |
| % calculated | 55.87 | 8.04 | 6.21 | 15.71 |
| % found | 55.59 | 8.14 | 6.25 | 15.98 |

EXAMPLE 2

4-Octahydro-2H-pyrido[1,2-a]pyrazin-2-yl-N-(3,4,5-trimethoxy-phenyl)butanamide dihydrochloride Step A: Ethyl 4-(octahydro-2H-pyrido[1,2-a]pyrazin-2-yl)-butyracetate 7 g of octahydro-2H-pyrido[1,2-a]pyrazine, 14 ml of ethyl 4-bromobutyrate and 14 g of potassium carbonate in 250 ml of acetonitrile are stirred for 24 hours at room temperature. The mineral salts are removed by filtration and the solvent is distilled off under a partial vacuum. The residue is taken up in 200 ml of 2N hydrochloric acid and washed with 200 ml of diethyl ether. The aqueous phase is then rendered alkaline with sodium hydrogen carbonate and extracted with dichloromethane. Drying over sodium sulphate and evaporation under a partial vacuum yield the expected product.

Step B: 4-(Octahydro-2H-pyrido[1,2-a]pyrazin-2-yl)butyric acid 11.2 g of the compound obtained in Step B are stirred in 100 ml of water, 11 ml of 1M sodium hydroxide solution and 100 ml of ethanol for 24 hours at 60° C. The solvent is then distilled off under a partial vacuum and the residue is dried at 60° C. in vacuo to yield the expected product.

| Elemental microanalysis: | | | |
|---|---|---|---|
| | C | H | N |
| % calculated | 58.05 | 8.52 | 11.28 |
| % found | 57.40 | 8.44 | 10.95 |

Step C: 4-Octahydro-2H-pyrido[1,2-a]pyrazin-2-yl-N-(3,4,5-trimethoxy-phenyl)butanamide dihydrochloride 1.2 g of the compound obtained in Step B, 1.05 g of 1-(3-dimethylaminopropyl)-3-ethylcarbodiimide hydrochloride and 0.92 g of 3,4,5-trimethoxyaniline in solution in 50 ml of dichloromethane and 1.75 ml of diisopropylethylamine are stirred, under argon, for 24 hours at room temperature. The reaction mixture is washed with 50 ml of water, decanted, dried over $Na_2SO_4$ and concentrated under a partial vacuum. The hydrochloride is then prepared in 20 ml of ethanol and 2 ml of an ethereal hydrogen chloride solution, enabling the expected product to be obtained.

Melting point: 230–232° C.

| Elemental microanalysis: | | | | |
|---|---|---|---|---|
| | C | H | N | Cl |
| % calculated | 56.53 | 7.79 | 9.42 | 11.92 |
| % found | 56.63 | 7.88 | 9.16 | 11.94 |

EXAMPLE 3

4-Octahydro-2H-pyrido[1,2-a]pyrazin-2-yl-N-phenylbutanamide dihydrochloride

The procedure is as for Example 2 using as substrate aniline and the compound obtained in Step B of Example 2.

Melting point: >250° C.

| Elemental microanalysis: | | | | |
|---|---|---|---|---|
| | C | H | N | Cl |
| % calculated | 57.75 | 7.81 | 11.22 | 18.94 |
| % found | 57.74 | 7.71 | 11.11 | 19.55 |

EXAMPLE 4

4-Octahydro-2H-pyrido[1,2-a]pyrazin-2-yl-N-(4-bromophenyl)-butanamide dihydrochloride The procedure is as for Example 2 using as substrate 4-bromoaniline and the compound obtained in Step B of Example 2.

Melting point: >250° C.

| Elemental microanalysis: | | | | |
|---|---|---|---|---|
| | C | H | N | Cl |
| % calculated | 47.70 | 6.23 | 9.27 | 15.64 |
| % found | 47.38 | 6.34 | 8.92 | 15.48 |

EXAMPLE 5

N-(4-Fluorophenyl)-4-octahydro-2H-pyrido[1,2-a]pyrazin-2-yl-butanamide dihydrochloride The procedure is as for Example 2 using as substrate 4-fluoroaniline and the compound obtained in Step B of Example 2.

Melting point: 243–244° C.

| Elemental microanalysis: | | | | |
|---|---|---|---|---|
| | C | H | N | Cl |
| % calculated | 55.10 | 7.19 | 10.71 | 18.07 |
| % found | 54.91 | 7.34 | 10.46 | 18.16 |

EXAMPLE 6

4-Octahydro-2H-pyrido[1,2-a]pyrazin-2-yl-N-(4-methylphenyl)-butanamide dihydrochloride The procedure is as for Example 2 using as substrate 4-methylaniline and the compound obtained in Step B of Example 2.

Melting point: 248–250° C.

| Elemental microanalysis: | | | | |
| --- | --- | --- | --- | --- |
| | C | H | N | Cl |
| % calculated | 58.76 | 8.05 | 10.82 | 18.26 |
| % found | 58.48 | 7.95 | 10.58 | 18.10 |

EXAMPLE 7

4-Octahydro-2H-pyrido[,2-a]pyrazin-2-yl-N-(4-trifluoromethyl-phenyl)butanamide dihydrochloride The procedure is as for Example 2 using as substrate 4-trifluoromethylaniline and the compound obtained in Step B of Example 2.

Melting point: >250° C.

| Elemental microanalysis: | | | | |
| --- | --- | --- | --- | --- |
| | C | H | N | Cl |
| % calculated | 51.59 | 6.38 | 9.50 | 16.03 |
| % found | 51.76 | 6.48 | 9.36 | 16.14 |

EXAMPLE 8

4-Octahydro-2H-pyrido[1,2-a]pyrazin-2-yl-N-(4-methoxyphenyl)-butanamide dihydrochloride The procedure is as for Example 2 using as substrate p-anisidine and the compound obtained in Step B of Example 2.

Melting point: 248–250° C.

| Elemental microanalysis: | | | | |
| --- | --- | --- | --- | --- |
| | C | H | N | Cl |
| % calculated | 56.43 | 7.73 | 10.39 | 17.53 |
| % found | 56.60 | 7.72 | 10.35 | 17.59 |

EXAMPLE 9

2-[4-(2,3-Dihydro-1H-indol-1-yl)4-oxobutyl]octahydro-2H-pyrido[1,2-a]pyrazine dihydrochloride The procedure is as for Example 2 using as substrate 2,3-dihydroindole and the compound obtained in Step B of Example 2.

Melting point: >250° C.

| Elemental microanalysis: | | | | |
| --- | --- | --- | --- | --- |
| | C | H | N | Cl |
| % calculated | 60.00 | 7.80 | 10.49 | 17.71 |
| % found | 59.72 | 7.77 | 10.28 | 17.85 |

EXAMPLE 10

4-Octahydro-2H-pyrido[1,2-a]pyrazin-2-yl-N-(4-tert-butyl-phenyl)butanamide dihydrochloride The procedure is as for Example 2 using as substrate 4-tert-butylaniline and the compound obtained in Step B of Example 2.

Melting point: >250° C.

| Elemental microanalysis: | | | | |
| --- | --- | --- | --- | --- |
| | C | H | N | Cl |
| % calculated | 61.39 | 8.66 | 9.76 | 16.47 |
| % found | 61.09 | 8.58 | 9.64 | 16.41 |

EXAMPLE 11

4-Octahydro-2H-pyrido[1,2-a]pyrazin-2-yl-N-(3,4-dimethoxy-phenyl)butanamide dihydrochloride The procedure is as for Example 2 using as substrate 3,4-dimethoxyaniline and the compound obtained in Step B of Example 2.

Melting point: >250° C.

| Elemental microanalysis: | | | | |
| --- | --- | --- | --- | --- |
| | C | H | N | Cl |
| % calculated | 55.30 | 7.66 | 9.67 | 16.32 |
| % found | 55.47 | 7.71 | 9.66 | 16.62 |

EXAMPLE 12

N-(1,3-Benzodioxol-5-yl)-4-octahydro-2H-pyrido[1,2-a]pyrazin-2-ylbutanamide dihydrochloride The procedure is as for Example 2 using as substrate benzo[1,3]dioxol-5-ylamine and the compound obtained in Step B of Example 2.

Melting point: >250° C.

| Elemental microanalysis: | | | | |
| --- | --- | --- | --- | --- |
| | C | H | N | Cl |
| % calculated | 54.55 | 6.99 | 10.04 | 16.95 |
| % found | 54.41 | 7.00 | 9.83 | 16.96 |

EXAMPLE 13

4-Octahydro-2H-pyrido[1,2-a]pyrazin-2-yl-N-(3-chlorophenyl)-butanamide dihydrochloride The procedure is as for Example 2 using as substrate 3-chloroaniline and the compound obtained in Step B of Example 2.
Melting point: >250° C.

Elemental microanalysis:

|  | C | H | N | Cl |
|---|---|---|---|---|
| % calculated | 52.89 | 6.90 | 10.28 | 26.02 |
| % found | 52.83 | 6.86 | 10.10 | 25.97 |

EXAMPLE 14

N-(3,5-Dichlorophenyl)-4-octahydro-2H-pyridol[1,2-a]pyrazin-2-ylbutanamide dihydrochloride The procedure is as for Example 2 using as substrate 3,5-dichloroaniline and the compound obtained in Step B of Example 2.
Melting point: >250° C.

Elemental microanalysis:

|  | C | H | N | Cl |
|---|---|---|---|---|
| % calculated | 48.78 | 6.14 | 9.48 | 31.99 |
| % found | 48.55 | 6.21 | 9.22 | 32.11 |

EXAMPLE 15

4-Octahydro-2H-pyrido[1,2-a]pyrazin-2-yl-N-(2-methoxyphenyl)-butanamide dihydrochloride The procedure is as for Example 2 using as substrate 2-methoxyaniline and the compound obtained in Step B of Example 2.
Melting point: >250° C.

Elemental microanalysis:

|  | C | H | N | Cl |
|---|---|---|---|---|
| % calculated | 56.43 | 7.73 | 10.39 | 17.53 |
| % found | 56.53 | 7.78 | 10.39 | 17.53 |

EXAMPLE 16

N-(4-Octahydro-2H-pyrido[1,2-a]pyrazin-2-ylbutyl)-N-(3,4,5-trimethoxyphenyl)amine trihydrochloride 1.0 g of the compound obtained in Step C of Example 2 is dissolved in 50 ml of tetra-hydrofuran and, under argon, 5 ml of a 1M solution of borane in tetrahydrofuran are added, and the mixture is then refluxed for 6 hours. After hydrolysis with 1 ml of 4N HCl and evaporation to dryness, the residue is dissolved in 5 ml of ethanol and 1 ml of ethereal hydrogen chloride to yield the expected product.
Melting point: 248–250° C.

Elemental microanalysis:

|  | C | H | N | Cl |
|---|---|---|---|---|
| % calculated | 51.80 | 7.88 | 8.63 | 21.84 |
| % found | 51.34 | 7.83 | 8.43 | 22.24 |

EXAMPLE 17

N-(4-Octahydro-2H-pyrido[1,2-a]pyrazin-2-ylbutyl)-N-phenylamine trihydrochloride The procedure is as for Example 16 using the compound obtained in Example 3 as substrate.
Melting point: >250° C.

Elemental microanalysis:

|  | C | H | N | Cl |
|---|---|---|---|---|
| % calculated | 54.48 | 8.13 | 10.59 | 26.80 |
| % found | 54.60 | 8.08 | 10.44 | 26.40 |

EXAMPLE 18

N-(4-Trifluorophenyl)-N-(4-octahydro-2H-pyrido[1,2-a]pyrazin-2-ylbutyl)amine trihydrochloride The procedure is as for Example 16 using the compound obtained in Example 7 as substrate.
Melting point: >250° C.

Elemental microanalysis:

|  | C | H | N | Cl |
|---|---|---|---|---|
| % calculated | 49.10 | 6.72 | 9.04 | 22.88 |
| % found | 49.14 | 6.92 | 8.85 | 23.08 |

EXAMPLE 19

N-(4-Bromophenyl)-N-(4-octahydro-2H-pyrido[1,2-a]pyrazin-2-ylbutyl)amine trihydrochloride The procedure is as for Example 16 using the compound obtained in Example 4 as substrate.
Melting point: >250° C.

Elemental microanalysis:

|  | C | H | N | Cl |
|---|---|---|---|---|
| % calculated | 45.45 | 6.57 | 8.83 | 22.36 |
| % found | 45.21 | 6.57 | 8.59 | 22.42 |

EXAMPLE 20

N-(4-Fluorophenyl)-N-(4-octahydro-2H-pyrido[1,2-a]pyrazin-2-ylbutyl)amine trihydrochloride The procedure is as for Example 16 using the compound obtained in Example 5 as substrate.

Melting point: >250° C.

| Elemental microanalysis: | | | | |
|---|---|---|---|---|
| | C | H | N | Cl |
| % calculated | 52.12 | 7.53 | 10.13 | 25.64 |
| % found | 52.46 | 7.43 | 9.98 | 25.47 |

EXAMPLE 21

N-(4-Methylphenyl)-N-(4-octahydro-2H-pyrido[1,2-a]pyrazin-2-ylbutyl)amine trihydrochloride The procedure is as for Example 16 using the compound obtained in Example 6 as substrate.

Melting point: >250° C.

| Elemental microanalysis: | | | | |
|---|---|---|---|---|
| | C | H | N | Cl |
| % calculated | 55.54 | 8.34 | 10.23 | 25.89 |
| % found | 55.83 | 8.29 | 9.98 | 25.64 |

EXAMPLE 22

N-(4-Methoxyphenyl)-N-(4-octahydro-2H-pyrido[1,2-a]pyrazin-2-ylbutyl)amine trihydrochloride The procedure is as for Example 16 using the compound obtained in Example 8 as substrate.

Melting point: >250° C.

| Elemental microanalysis: | | | | |
|---|---|---|---|---|
| | C | H | N | Cl |
| % calculated | 53.46 | 8.03 | 9.84 | 24.92 |
| % found | 53.14 | 8.15 | 9.49 | 24.11 |

EXAMPLE 23

2-[4-(2,3-Dihydro-1H-indol-1-yl)butyl]octahydro-2H-pyrido[1,2-a]pyrazine trihydrochloride The procedure is as for Example 16 using the compound obtained in Example 9 as substrate.

Melting point: >250° C.

| Elemental microanalysis: | | | | |
|---|---|---|---|---|
| | C | H | N | Cl |
| % calculated | 56.94 | 7.88 | 9.96 | 25.21 |
| % found | 57.81 | 8.15 | 9.88 | 24.98 |

EXAMPLE 24

N-(4-Tert-butyl-phenyl)-N-(4-octahydro-2H-pyrido[1,2-a]pyrazin-2-ylbutyl)amine trihydrochloride The procedure is as for Example 16 using the compound obtained in Example 10 as substrate.

Melting point: >250° C.

| Elemental microanalysis: | | | | |
|---|---|---|---|---|
| | C | H | N | Cl |
| % calculated | 58.34 | 8.90 | 9.28 | 23.48 |
| % found | 58.52 | 8.94 | 9.37 | 23.53 |

EXAMPLE 25

N-(3,4-Dimethoxyphenyl)-N-(4-octahydro-2H-pyrido[1,2-a]pyrazin-2-ylbutyl)amine trihydrochloride The procedure is as for Example 16 using the compound obtained in Example 11 as substrate.

Melting point: >250° C.

| Elemental microanalysis: | | | | |
|---|---|---|---|---|
| | C | H | N | Cl |
| % calculated | 52.58 | 7.94 | 9.20 | 23.28 |
| % found | 52.50 | 7.84 | 9.36 | 23.20 |

EXAMPLE 26

N-(4-Octahydro-2H-pyrido[1,2-a]pyrazin-2-ylbutyl)-1,3-benzodioxol-5-amine trihydrochloride The procedure is as for Example 16 using the compound obtained in Example 12 as substrate.

Melting point: 248–250° C.

| Elemental microanalysis: | | | | |
|---|---|---|---|---|
| | C | H | N | Cl |
| % calculated | 51.77 | 7.32 | 9.53 | 24.13 |
| % found | 51.15 | 7.41 | 9.16 | 24.15 |

EXAMPLE 27

N-(3-Chlorophenyl)-N-(4-octahydro-2H-pyrido[1,2-a]pyrazin-2-ylbutyl)amine trihydrochloride The procedure is as for Example 16 using the compound obtained in Example 13 as substrate.
Melting point: >250° C.

| Elemental microanalysis: | | | | |
|---|---|---|---|---|
| | C | H | N | Cl |
| % calculated | 50.13 | 7.25 | 9.74 | 32.88 |
| % found | 50.01 | 7.28 | 9.52 | 32.86 |

EXAMPLE 28

N-(3,5-Dichlorophenyl)-N-(4-octahydro-2H-pyrido[1,2-a]pyrazin-2-ylbutyl)amine trihydrochloride The procedure is as for Example 16 using the compound obtained in Example 14 as substrate.
Melting point: >250° C.

| Elemental microanalysis: | | | | |
|---|---|---|---|---|
| | C | H | N | Cl |
| % calculated | 46.42 | 6.49 | 9.02 | 38.06 |
| % found | 46.67 | 6.53 | 8.91 | 37.49 |

EXAMPLE 29

N-(2-Methoxyphenyl)-N-(4-octahydro-2H-pyrido[1,2-a]pyrazin-2-ylbutyl)amine trihydrochloride The procedure is as for Example 16 using the compound obtained in Example 15 as substrate.
Melting point: >250° C.

| Elemental microanalysis: | | | | |
|---|---|---|---|---|
| | C | H | N | Cl |
| % calculated | 53.46 | 8.03 | 9.84 | 24.92 |
| % found | 53.31 | 8.15 | 9.65 | 24.92 |

EXAMPLE 30

N-(4-Chlorophenyl)-N-(4-octahydro-2H-pyrido[1,2-a]pyrazin-2-ylbutyl)amine trihydrochloride Step A: N-(4-Chlorophenyl)-4-(octahydro-2H-pyrido[1,2-a]pyrazin-2-yl)-butyramide
The procedure is as for Example 2 using as substrate 4-chloroaniline and the compound obtained in Step B of Example 2.

Step B: N-(4-Chlorophenyl)-N-(4-octahydro-2H-pyrido[1,2-a]pyrazin-2-ylbutyl)amine trihydrochloride
The procedure is as for Example 16 using the compound obtained in the preceding Step A as substrate.
Melting point: >250° C.

| Elemental microanalysis: | | | | |
|---|---|---|---|---|
| | C | H | N | Cl |
| % calculated | 50.13 | 7.25 | 9.74 | 32.88 |
| % found | 50.19 | 7.42 | 9.66 | 32.89 |

EXAMPLE 31

N-(2-Chlorophenyl)-N-(4-octahydro-2H-pyrido[1,2-a]pyrazin-2-ylbutyl)amine trihydrochloride Step A: N-(2-Chlorophenyl)-N-(4-octahydro-2H-pyrido[1,2-a]pyrazin-2-yl)-butyramide
The procedure is as for Example 2 using as substrate 2-chloroaniline and the compound obtained in Step B of Example 2.

Step B: N-(2-Chlorophenyl)-N-(4-octahydro-2H-pyrido[1,2-a]pyrazin-2-ylbutyl)amine trihydrochloride
The procedure is as for Example 16 using the compound obtained in the preceding Step A as substrate.
Melting point: >250° C.

| Elemental microanalysis: | | | | |
|---|---|---|---|---|
| | C | H | N | Cl |
| % calculated | 52.34 | 7.44 | 10.17 | 30.04 |
| % found | 51.92 | 7.69 | 9.86 | 29.93 |

EXAMPLE 32

N-(3,4-Dichlorophenyl)-N-(4-octahydro-2H-pyrido[1,2-a]pyrazin-2-ylbutyl)amine trihydrochloride Step A: N-(3,4-Dichlorophenyl)-4(octahydro-2H-pyrido[1,2-a]pyrazin-2-yl)-butyramide
The procedure is as for Example 2 using as substrate 3,4-dichloroaniline and the compound obtained in Step B of Example 2.

Step B: N-(3,4-Dichlorophenyl)-N-(4-octahydro-2H-pyrido[1,2-a]pyrazin-2-ylbutyl)amine trihydrochloride
The procedure is as for Example 16 using the compound obtained in the preceding Step A as substrate.
Melting point: >250° C.

| Elemental microanalysis: | | | | |
|---|---|---|---|---|
| | C | H | N | Cl |
| % calculated | 46.42 | 6.49 | 9.02 | 38.06 |
| % found | 46.50 | 6.51 | 9.01 | 37.40 |

EXAMPLE 33

N-Benzyl-N-(4-octahydro-2H-pyrido[1,2-a]pyrazin-2-ylbutyl)-N-(3,4,5-trimethoxyphenyl)amine trihydrochloride

Step A: N-Benzyl-4-(octahydro-2H-pyrido[1,2-a]pyrazin-2-yl)-N-(3,4,5-trimethoxyphenyl)-butyramide The procedure is as for Example 2 using as substrate benzyl-(3,4,5-trimethoxyphenyl)-amine and the compound obtained in Step B of Example 2.

Step B: N-Benzyl-N-(4-octahydro-2H-pyrido[1,2-a]pyrazin-2-ylbutyl)-N-(3,4,5-trimethoxyphenyl)amine trihydrochloride The procedure is as for Example 16 using the compound obtained in the preceding Step A as substrate.

Melting point: 220–222° C.

| Elemental microanalysis: | | | | |
| --- | --- | --- | --- | --- |
|  | C | H | N | Cl |
| % calculated | 58.28 | 7.69 | 7.28 | 18.43 |
| % found | 59.44 | 7.80 | 7.51 | 17.51 |

EXAMPLE 34

3,4,5-Trimethoxy-N-(4-octahydro-2H-pyrido[1,2-a]pyrazin-2-ylbutyl)-N-phenylaniline trihydrochloride

Step A: N-Phenyl-4-(octahydro-2H-pyrido[1,2-a]pyrazin-2-yl)-N-(3,4,5-trimetlioxyphenyl)-butyramide The procedure is as for Example 2 using as substrate phenyl-(3,4,5-trimethoxyphenyl)amine and the compound obtained in Step B of Example 2.

Step B: 3,4,5-Trimethoxy-N-(4-octahydro-2H-pyrido[1,2-a]pyrazin-2-ylbutyl)-N-phenylaniline The procedure is as for Example 16 using the compound obtained in the preceding Step A as substrate.

Melting point: 201–202° C.

| Elemental microanalysis: | | | | |
| --- | --- | --- | --- | --- |
|  | C | H | N | Cl |
| % calculated | 59.53 | 7.68 | 7.71 | 16.27 |
| % found | 59.96 | 7.72 | 8.10 | 16.20 |

EXAMPLE 35

N-Methyl4-octahydro-2H-pyrido[1,2-a]pyrazin-2-yl-N-(3,4,5-trimethoxyphenyl)butanamide dihydrochloride

0.9 g of the compound obtained in Example 2 is dissolved in 50 ml of tetrahydrofuran and, under argon, there are added 0.265 g of potassium tert-butoxide and then, after 1 hour's stirring, 0.15 ml of methyl iodide. Stirring is maintained for 1 hour and the solvent is removed in vacuo. The residue is taken up in a mixture of water/dichloromethane, extracted, decanted and then dried over $Na_2SO_4$ and evaporated to dryness in vacuo. The product is converted to the hydrochloride using ethanolic hydrogen chloride.

Melting point: 185–186° C.

| Elemental microanalysis: | | | | |
| --- | --- | --- | --- | --- |
|  | C | H | N | Cl |
| % calculated | 55.23 | 7.79 | 8.78 | 14.82 |
| % found | 55.05 | 7.87 | 8.52 | 14.72 |

EXAMPLE 36

N-Methyl-N-(4-octahydro-2H-pyrido[1,2-a]pyrazin-2-ylbutyl)-N-(3,4,5-trimethoxyphenyl)amine trihydrochloride

10 ml of a 1M solution of borane in tetrahydrofuran are added to 0.4 g of the compound obtained in Example 35 in solution, under argon, in 50 ml of tetrahydroftiran and the mixture is refluxed for 8 hours. After hydrolysis with 2 ml of 4N hydrochloric acid, evaporation to dryness and conversion to the base, the hydrochloride is prepared using an ethanolic hydrogen chloride solution.

Melting point: 214–215° C.

| Elemental microanalysis: | | | | |
| --- | --- | --- | --- | --- |
|  | C | H | N | Cl |
| % calculated | 52.75 | 8.05 | 8.39 | 21.23 |
| % found | 53.20 | 8.01 | 8.53 | 21.42 |

EXAMPLE 37

3,4,5-Trimethoxy-N-(3-octahydro-2H-pyrido[1,2-a]pyrazin-2-ylpropyl)benzamide dihydrochloride

Step A: 2-(Octahydro-2H-pyrido[1,2-a]pyrazin-2-yl)acetonitrile 8 g of octahydro-2H-pyrido[1,2-a]pyrazine and 12 ml of acrylonitrile are refluxed for 48 hours in 150 ml of acetonitrile. The solvent is then removed in vacuo to yield 11 g of a pale yellow oil.

Step B: 3-(Octahydro-2H-pyrido[1,2-a]pyrazin-2-yl)propanamine 4 g of the compound obtained in Step A, 0.4 g of $PtO_2$, 30 ml of methanolic hydrogen chloride and 100 ml of methanol are hydrogenated in an autoclave, under 5 bars of hydrogen pressure for 8 hours at room temperature. The catalyst is then removed by filtration and the filtrate is evaporated and then converted to the base to yield the expected product.

Step C: 3,4,5-Trimethoxy-N-(3-octahtydro-2H-pyrido[1,2-a]pyrazin-2-ylpropyl)benzamide dihydrochloride 2.1 g of the compound obtained in Step B, 2.3 g of 3,4,5 trimethoxybenzoic acid, 3.8 ml of diisopropylethylamine and 2.1 g of 1-(3-dimethylaminopropyl)-3-ethylcarbodiimide hydrochloride in 200 ml of dichloromethane are stirred for 48 hours at room temperature under argon. The mixture is then washed with 100 ml of water, dried over $Na_2SO_4$, evaporated to dryness, purified over a chromatography column eluted with a mixture of dichloromethane/methanol (98/2) and converted to its hydrochloride in ethanol.

Melting point: 224–225° C.

Elemental microanalysis:

|  | C | H | N | Cl |
|---|---|---|---|---|
| % calculated | 54.31 | 7.61 | 9.05 | 15.27 |
| % found | 54.13 | 7.42 | 9.10 | 15.37 |

EXAMPLE 38

N-(3-Octahydro-2H-pyrido[1,2-a]pyrazin-2-ylpropyl)-N-(3,4,5-trimethoxybenzyl)amine tritydrochloride 8 ml of a 1M solution of DIBAL in toluene are added, under argon, to 0.45 g of the compound obtained in Step C of Example 37 in 50 ml of tetrahydrofuran, and the mixture is stirred for 20 hours. After hydrolysis with 2 ml of 4N hydrochloric acid and removal of the solvent by evaporation under a partial vacuum, the residue is taken up in 50 ml of dichloromethane and 50 ml of 5% sodium hydrogen carbonate in water. After extraction and decanting, the organic phase is dried over $Na_2SO_4$ and then concentrated to dryness. The residue is converted to the hydrochloride using ethanolic hydrogen chloride.

Melting point: 247–248° C.

Elemental microanalysis:

|  | C | H | N | Cl |
|---|---|---|---|---|
| % calculated | 51.80 | 7.87 | 8.63 | 21.84 |
| % found | 51.46 | 7.81 | 8.57 | 21.80 |

EXAMPLE 39

2-[4-(1H-Indol-1-yl)butyl]octahydro-2H-pyrido[1,2-a]pyrazine dihydrochloride

Step A: 1-(4-Bromo-butyl)-1H-indole

A solution of 6 g of indole in 150 ml of dimethylformamide is provided with sodium using 2 g of 60% sodium hydride in oil, and then 11 ml of 1,4-dibromobutane are added rapidly and the mixture is stirred overnight at room temperature. After distilling off the dimethylformamide, the residue is taken up in a mixture of water/dichloromethane, extracted and decanted. The organic phase is dried over $Na_2SO_4$ and concentrated in vacuo. The residue is purified over a silica column (dichloromethane/heptane:5/5) to yield the expected compound.

Step B: 2-[4-(1H-Indol-1-yl)butyl]octahydro-2H-pyrido[1,2-a]pyrazine dihydrochloride 1.2 g of the compound obtained in Step A, 0.7 g of octahydro-2H-pyrido[1,2-a]pyrazine and 1.4 g of potassium carbonate are stirred for 24 hours in 60 ml of ethanol. The mineral salts are then removed by filtration and the filtrate is concentrated to dryness in vacuo. The resulting compound is converted to the hydrochloride in a mixture of ethanol/hydrochloric acid/diisopropyl ether, enabling the expected product to be isolated.

Melting point: >250° C.

Elemental microanalysis:

|  | C | H | N | Cl |
|---|---|---|---|---|
| % calculated | 62.49 | 8.13 | 10.93 | 18.85 |
| % found | 62.13 | 8.14 | 10.85 | 18.52 |

EXAMPLE 40

N-(4-Octahydro-2H-pyrido[1,2-a]pyrazin-2-ylbutyl)-N-(3,4,5-trimethoxyphenyl)acetamide dihydrochloride 0.16 ml of acetyl chloride is added, at 0° C., to 0.44 g of the compound obtained in Example 16 in solution in 50 ml of dichloromethane and 0.16 ml of triethylamine, and the mixture is stirred for 2 hours. The solution is washed with 25 ml of a 5% sodium hydrogen carbonate solution, dried over sodium sulphate, evaporated to dryness and then purified over a silica column eluted with a mixture of $CH_2Cl_2$/MeOH (95/5). The purified compound is converted to the hydrochloride using an ethanolic hydrogen chloride solution.

Melting point: >250° C.

Elemental microanalysis:

|  | C | H | N | Cl |
|---|---|---|---|---|
| % calculated | 56.09 | 7.98 | 8.53 | 14.40 |
| % found | 55.71 | 7.96 | 8.27 | 14.44 |

EXAMPLE 41

N-(5-Octahydro-2H-pyrido[1,2-a]pyrazin-2-ylpentyl)-N-(3,4,5-trimethoxyphenyl)amine trihydrochloride Step A: Ethyl 4-(3,4,5-trimethoxyphenylcarbamoyl)-butyrate 8.2 ml of ethylglutaric acid chloride are added dropwise to a solution, cooled to 0–5° C., of 3,4,5-trimethoxyaniline in 150 ml of dichloromethane and 7.2 ml of triethylamine. After 3 hours' stirring, the reaction mixture is washed with 100 ml of water, decanted, dried over $Na_2SO_4$ and evaporated to dryness to yield the expected product.

Step B: 4-(3,4,5-Trimethoxy-phenylcarbamoyl)-butyric acid

A solution of 8 g of the compound obtained in Step A, 50 ml of 1M sodium hydroxide solution, 50 ml of water and 100 ml of ethanol is stirred for 6 hours at 50° C. The ethanol is then removed by distillation under a partial vacuum. The residual solution is rendered acidic by the addition of 1M hydrochloric acid and extracted with dichloromethane. The combined organic phases are dried with $Na_2SO_4$ and evaporated to dryness to yield a colourless oil (quantitative yield).

Step C: 5-(Octahydro-pyrido[1,2-a]pyrazin-2-yl)-5-oxo-(3,4,5-trimethoxy-phenyl)pentanamide A solution of 3 g of the compound obtained in Step C, 1.4 g of octahydro-2H-pyrido[1,2-a]pyrazine, 2 g of 1-(3-dimethylaminopropyl)-3-ethylcarbodiimide hydrochloride, and 2 ml of diisopropylethylamine in 150 ml of dichloromethane is stirred for 24 hours at room temperature, and then washed with 150 ml of water, decanted, dried over $Na_2SO_4$ and evaporated to dryness to yield a colourless oil.

Step D: N-(5-Octahydro-2H-pyrido[1,2-a]pyrazin-2-yl-pentyl)-N-(3,4,5-trimethoxyphenyl)amine trihydrochloride 15 ml of a 1M solution of borane in tetrahydrofuran are added to a solution, placed under argon, of 1.5 g of the compound obtained in Step C in 100 ml of tetrahydrofuran, and the mixture is refluxed for 8 hours at 50° C., and then hydrolysed with 5 ml of 4N hydrochloric acid. After removal of the solvent by evaporation, and then conversion to the base, the hydrochloride is obtained using an ethanolic hydrogen chloride solution.

Melting point: 226–228° C.

| Elemental microanalysis: | | | | |
|---|---|---|---|---|
| | C | H | N | Cl |
| % calculated | 52.75 | 8.05 | 8.39 | 21.23 |
| % found | 53.40 | 8.06 | 8.27 | 20.13 |

EXAMPLE 42

3-Octahydro-2H-pyrido[1,2-a]pyrazin-2-yl-N-(3,4,5-trimethoxy-phenyl)propionamide dihydrochloride Step A: Ethyl 3-(octahydro-2H-pyrido[1,2-a]pyrazin-2-yl)propionate A solution of 7 g of octahydro-2H-pyrido[1,2-a]pyrazine and 15 ml of ethyl acrylate in 100 ml of acetonitrile is refluxed for 24 hours and then concentrated to dryness in vacuo to yield the expected product.

| Elemental microanalysis: | | | |
|---|---|---|---|
| | C | H | N |
| % calculated | 64.97 | 10.06 | 11.66 |
| % found | 64.34 | 10.08 | 11.47 |

Step B: 3-(Octahydro-2H-pyrido[1,2-a]pyrazin-2-yl)propionic acid

A solution of 6.0 g of the compound obtained in Step A in 50 ml of ethanol and 25 ml of a 1M sodium hydroxide solution is heated for 5 hours at 50° C. and then concentrated to dryness in vacuo and dried in the presence of $P_2O_5$ to yield the expected compound.

Step C: 3-Octahydro-2H-pyrido[1,2-a]pyraziin-2-yl-N-(3,4,5-trimethoxy-phenyl)propionamide dihydrochloride A solution of 6.0 g of the compound obtained in Step B, 4.8 g of 1-(3-dimethylamino-propyl)-3-ethylcarbodiimide hydrochloride, 4.8 g of trimethoxyaniline and 4.7 ml of diusopropylethylamine, in 200 ml of dichloromethane is stirred for 24 hours, and then washed with 100 ml of water, decanted, dried over $Na_2SO_4$ and finally evaporated to dryness to yield the expected product in the form of a base. The hydrochloride is prepared using an ethereal hydrogen chloride solution.

Melting point: 249–250° C.

| Elemental microanalysis: | | | | |
|---|---|---|---|---|
| | C | H | N | Cl |
| % calculated | 53.33 | 7.38 | 9.33 | 15.74 |
| % found | 53.09 | 7.39 | 9.18 | 16.21 |

EXAMPLE 43

N-(3-Octahydro-2H-pyrido[1,2-a]pyrazin-2-ylpropyl)-N-(3,4,5-trimethoxyphenyl)amine trihydrochloride A solution of 1.5 g of the compound obtained in Step C of Example 42 in 100 ml of tetrahydrofuran and 15 ml of a 1M solution of borane in tetrahydrofuran is heated for 6 hours at reflux, and then hydrolysed with 5 ml of 4N hydrochloric acid. After removal of the solvent by evaporation, and then conversion to the base, the hydrochloride is prepared by crystallisation from an ethanolic hydrogen chloride solution.

Melting point: 226–228° C.

| Elemental microanalysis: | | | | |
|---|---|---|---|---|
| | C | H | N | Cl |
| % calculated | 50.80 | 7.67 | 8.89 | 22.49 |
| % found | 51.37 | 7.99 | 8.87 | 22.40 |

EXAMPLE 44

2-[4-(3,4,5-Trimethoxybenzyloxy)butyl]octahydro-2H-pyrido[1,2-a]pyrazine dihydrochloride Step A: Ethyl 3-(octahydro-2H-pyrido[1,2-a]pyrazin-2-yl)propanoate A solution of 3.5 g of octahydro-2H-pyrido[1,2-a]pyrazine and 8 ml of ethyl acrylate in 50 ml of acetonitrile is refluxed for 24 hours. The solvent is removed in vacuo to yield the expected product.

| Elemental microanalysis: | | | |
|---|---|---|---|
| | C | H | N |
| % calculated | 64.97 | 10.06 | 11.66 |
| % found | 64.34 | 10.08 | 11.47 |

Step B: 3-(Octahydro-2H-pyrido[1,2-a]pyrazin-2-yl)propanol 1 g of $LiAlH_4$ is added in portions to a solution of 3 g of the compound obtained in Step A, in 100 ml of tetrahydrofuran, and then the reaction mixture is stirred for 8 hours, subsequently hydrolysed, filtered and finally evaporated to dryness.

Step C: 3-(Octahydro-2H-pyrido[1,2-a]pyrazin-2-yl)propanol 4-toluene-sulphonate

A solution of 4.5 g of the compound obtained in Step B, 2.5 ml of pyridine, and 4.8 g of tosyl chloride in 100 ml of dichloromethane is stirred for 24 hours at room temperature, and then washed with 100 ml of water and finally purified over a silica gel chromatography column, eluted with a mixture of $CH_2Cl_2$/MeOH (95/5), enabling the expected product to be isolated.

Step D: 2-[4-(3,4,5-Trimethoxybenzyloxy)butyl]octahydro-2H-pyrido[1,2-a]pyrazine dihydrochloride A solution of 0.9 g of 3,4,5-trimethoxybenzyl alcohol in 100 ml of tetrahydrofuran is provided with sodium using 0.25 g of 60% sodium hydride in oil. When the evolution of hydrogen has ceased, 1.6 g of the compound obtained in Step C are added in 10 ml of tetrahydrofuran, and the reaction mixture is stirred for 8 hours, and then washed with 100 ml of water, dried over $Na_2SO_4$ and evaporated to dryness. Purification over silica gel eluted with a mixture of $CH_2Cl_2$/MeOH (98/2) enables the expected product to be isolated, which is then converted to the hydrochloride using an ethanolic hydrogen chloride solution.

Melting point: 182–183° C.

| | Elemental microanalysis: | | | |
|---|---|---|---|---|
| | C | H | N | Cl |
| % calculated | 55.87 | 8.04 | 6.21 | 15.71 |
| % found | 55.24 | 7.94 | 6.34 | 16.04 |

EXAMPLE 45

2-[4-(3,4,5-Trimethoxy-phenylsulphanyl)butyl]octahydro-2H-pyrido[1,2-a]pyrazine dihydrochloride Step A: Triisopropyl-(3,4,5-trimethoxyphenylsulphanyl)-silane 1.12 g of sodium hydride are added to a solution of 5 g of triisopropylsilanethiol in 100 ml of tetrahydrofuran. When the evolution of hydrogen has ceased, 2.4 g of $Pd(PPh_3)_4$, 100 ml of toluene and 6.9 g of 1-bromo-3,4,5-trimethoxybenzene are added, and the reaction mixture is refluxed for 2 hours, and then evaporated in vacuo. Chromatography over silica gel eluted with a mixture of $CH_2Cl_2$/heptane (70/30) enables the expected product to be isolated.

| | Elemental microanalysis: | | |
|---|---|---|---|
| | C | H | S |
| % calculated | 60.63 | 9.04 | 8.99 |
| % found | 61.12 | 9.19 | 8.38 |

Step B: Ethyl 4-(3,4,5-trimethoxy-phenylsulphanyl)butyrate

A suspension of 1.78 g of the compound obtained in Step A, 0.835 g of CsF and 1.1 g of ethyl 4-bromobutyrate in 80 ml of dimethylformamide is stirred, under argon, for 3 hours. After removal of the solvent by distillation, the residue is taken up in a mixture of water/dichloromethane, decanted and then dried over sodium sulphate. Chromatography over silica gel eluted with dichloromethane enables the expected product to be isolated.

Step C: 4-(3,4,5-Trimethoxy-phenylsulphanyl)butanoic acid

A solution of 1.6 g of the compound obtained in Step B in 25 ml of 1M sodium hydroxide solution and 25 ml of methanol is stirred for 4 hours at 50° C., and then distilled under a partial vacuum, rendered acidic with 25 ml of 1M hydrochloric acid and extracted with dichloromethane. The combined organic phases are dried over sodium sulphate and then evaporated to dryness, enabling the expected product to be isolated.

Melting point: 88–90° C.

| | Elemental microanalysis: | | |
|---|---|---|---|
| | C | H | S |
| % calculated | 54.53 | 6.34 | 11.20 |
| % found | 54.75 | 6.48 | 11.48 |

Step D: 1-(Octahydro-2H-pyrido[1,2-a]pyrazin-2-yl)-4-(3,4,5-trimethoxy-phenylsulphanyl)-butan-1-one The product is obtained in accordance with the procedure of Step C of Example 1, using the compound obtained in the preceding Step C as substrate.

Step E: 2-[4-(3,4,5-Trimethoxyphenylsulphanyl)butyl]octahydro-2H-pyrido-[1,2-a]pyrazine dihydrochloride A solution of 0.9 g of the compound obtained in Step D, 40 ml of tetrahydrofuran and 5 ml of a 1M solution of borane in tetrahydrofuran is refluxed for 8 hours, and then hydrolysed with 2 ml of 4N hydrochloric acid. After evaporation and conversion to the base, crystallisation of the salt from an ethanolic hydrogen chloride solution enables the expected product to be isolated.

Melting point: 215–216° C.

| | Elemental microanalysis: | | | | |
|---|---|---|---|---|---|
| | C | H | N | S | Cl |
| % calculated | 53.95 | 7.76 | 5.99 | 6.86 | 15.17 |
| % found | 54.29 | 7.91 | 5.69 | 6.64 | 14.97 |

EXAMPLE 46

3-(Octahydro-2H-pyrido[1,2-a]-pyrazin-2-yl)-1-(3,4,5-trimethoxy-phenyl)-pentan-1-one dihydrochloride Step A: Tributyl-(3,4,5-trimethoxyphenyl)stannane A solution of 8 g of 1-bromo-3,4,5-trimethoxybenzene, 25 ml of hexabutyldistannane and 1.8 g of $Pd(PPh_3)_4$ in 200 ml of toluene is refluxed, under argon, for 6 hours and then concentrated to dryness. The residue is purified by chromatography over silica gel eluted with dichloromethane, which enables the expected product to be isolated.

Step B: 5-Bromo-1-(3,4,5-trimethoxyphenyl)-pentan-1-one

A solution of 8.5 g of the compound obtained in Step A, 3.2 ml of 5-bromopentanoyl chloride, 0.3 g of $Pd_2(dba)_3$ and 250 ml of toluene is refluxed for 6 hours, and then cooled and evaporated in vacuo. The residue is purified by chromatography over silica gel eluted with dichloromethane, enabling the expected product to be isolated.

Step C: 3-(Octahydro-2H-pyrido[1,2-a]-pyrazin-2-yl)-1-(3,4,5-trimethoxy-phienyl)-pentan-1-one dihydrochloride A suspension of 1.5 g of the compound obtained in Step B, 0.7 g of octahydro-2H-pyrido[1,2-a]pyrazine and 1.4 g of potassium carbonate in 60 ml of acetonitrile is stirred for 24 hours at room temperature. The mineral salts are removed by filtration and the solvent is removed by distillation in vacuo.

The resulting base is converted to a salt using an ethanolic hydrogen chloride solution, enabling the expected product to be isolated.

Melting point: >250° C.

| Elemental microanalysis: | | | | |
|---|---|---|---|---|
| | C | H | N | Cl |
| % calculated | 57.02 | 7.83 | 6.04 | 15.30 |
| % found | 56.63 | 7.62 | 6.06 | 15.50 |

EXAMPLE 47

5-Octahydro-2H-pyrido[1,2-a]pyrazin-2-yl-1-(3,4,5-trimethoxy-phenyl)-1-pentanol dihydrochloride 0.1 g of $NaBH_4$ is added, in the course of one hour, to a solution of 0.5 g of the compound obtained in Step C of Example 46 in 30 ml of methanol, and the mixture is then evaporated to dryness in vacuo. A salt is crystallised from an ethanolic hydrogen chloride solution, enabling the expected product to be isolated.

Melting point: 184–185° C.

| Elemental microanalysis: | | | | |
|---|---|---|---|---|
| | C | H | N | Cl |
| % calculated | 56.77 | 8.23 | 6.02 | 15.23 |
| % found | 56.32 | 8.19 | 6.00 | 15.16 |

EXAMPLE 48

N-(4-octahydro-2H-pyrido[1,2-a]pyrazin-2-ylbutyl)-N-(3,4,5-trimethoxyphenyl)amine trihydrochloride, enantiomer α

EXAMPLE 49

N-(4-octahydro-2H-pyrido[1,2-a]pyrazin-2-ylbutyl)-N-(3,4,5-trimethoxyphenyl)amine trihydrochloride, enantiomer β

The compounds of examples 48 and 49 are obtained from 0.2 g of the compound of Example 16 which are separated over a CHIRALPAK AD chiral chromatography column. The hydrochloride is obtained by the action of an ethanolic hydrogen chloride solution.

Enantiomer α
 Optical purity: >99%
 Melting point: 248–250° C.

| Elemental microanalysis: | | | | |
|---|---|---|---|---|
| | C | H | N | Cl |
| % calculated | 51.80 | 7.87 | 8.63 | 21.84 |
| % found | 52.45 | 7.54 | 8.58 | 20.78 |

Enantiomer β
 Optical purity: 98.4%
 Melting point: 248–250° C.

| Elemental microanalysis: | | | | |
|---|---|---|---|---|
| | C | H | N | Cl |
| % calculated | 51.80 | 7.87 | 8.63 | 21.84 |
| % found | 52.75 | 7.60 | 8.09 | 20.54 |

EXAMPLE 50

2-[4-(3,4,5-trimethoxyphenoxy)-butyl]octahydro-2H-pyrido[1,2-a]pyrazine dihydrochloride, enantiomer α

EXAMPLE 51

2-[4-(3,4,5-trimethoxyphenoxy)-butyl]octahydro-2H-pyrido[1,2-a]pyrazine dihydrochloride, enantiomer β

The compounds of examples 50 and 51 are obtained from 0.2 g the compound of Example 1 which are separated over a CHIRALPAK AD chiral chromatography column. The hydrochloride is obtained by the action of an ethanolic hydrogen chloride solution.

Enantiomer α
 Optical purity: >99%
 Melting point: 220–221° C.

| Elemental microanalysis: | | | | |
|---|---|---|---|---|
| | C | H | N | Cl |
| % calculated | 55.87 | 8.04 | 6.21 | 15.71 |
| % found | 55.54 | 7.77 | 6.23 | 16.04 |

Enantiomer β
 Optical purity: 98.4%
 Melting point: 220–221° C.

| Elemental microanalysis: | | | | |
|---|---|---|---|---|
| | C | H | N | Cl |
| % calculated | 55.87 | 8.04 | 6.21 | 15.71 |
| % found | 55.24 | 7.86 | 6.01 | 15.78 |

EXAMPLE 52

2-[4-(3,4-Dihydro-1(2H)-quinolyl)butyl]octahydro-2H-pyrido-[1,2-a]pyrazine trihydrochloride Step A: 2-[4-(3,4-Dihydro-1(2H)-quinolyl)-4-oxobutyl]octahydro-2H-pyrido-[1,2-a]pyrazine The procedure is as for Example 2 using as substrate 3,4-dihydro-2H-quinoline and the compound obtained in Step B of Example 2.

Step B: 2-[4-(3,4-Dihydro-1(2H)-quinolyl)butyl]octahydro-2H-pyrido[1,2-a]pyrazine trihydrochloride The procedure is as for Example 23 using the compound obtained in the preceding Step A as substrate.
Melting point: 246–247° C.

Elemental microanalysis:

|  | C | H | N | Cl |
|---|---|---|---|---|
| % calculated | 57.73 | 8.31 | 9.62 | 24.34 |
| % found | 58.25 | 8.47 | 9.58 | 24.15 |

EXAMPLE 53

2-[4-(1H-Benzimidazol-1-yl)butyl]octahydro-2H-pyrido[1,2-a]pyrazine trihydrochloride Step A: 1-(4-Bromobutyl)-1H-benzimidazole
A solution of 5.9 g of benzimidazole in 150 ml of dimethylformamide is provided with sodium using 2 g of 60% sodium hydride in oil, and then 11 ml of 1,4-dibromobutane are added and the mixture is stirred overnight at room temperature. After distilling off the dimethylformamide, the residue is taken up in a mixture of water/dichloromethane, extracted and decanted. The organic phase is dried over $Na_2SO_4$ and concentrated in vacuo. The residue is purified over a silica column (dichloromethane/methanol: 95/5) to yield the expected product.
Step B: 2-[4-(1H-Benzimidazol-1-yl)butyl]octahydro-2H-pyrido[1,2-a]pyrazine trihydrochloride The procedure is as for Example 39 using the compound obtained in the preceding Step A.
Melting point: 244–245° C.

Elemental microanalysis:

|  | C | H | N | Cl |
|---|---|---|---|---|
| % calculated | 54.10 | 7.41 | 13.28 | 25.21 |
| % found | 54.04 | 7.36 | 13.17 | 25.04 |

EXAMPLE 54

4-[(4-Octahydro-2H-pyrido[1,2-a]pyrazin-2-ylbutyl)amino]benzonitrile difumarate 0.3 g of the compound obtained in Example 19, 45 mg of $Zn(CN)_2$ and 60 mg of tetrakis-triphenylphosphine palladium in solution in 40 ml of dimethylformamide are heated at 80° C., under argon, for 24 hours. After distilling off the dimethylformamide, the residue is purified over a silica column (dichloromethane/methanol:95/5) to yield the expected product.
Melting point: 188–190° C.

Elemental microanalysis:

|  | C | H | N |
|---|---|---|---|
| % calculated | 59.55 | 6.66 | 10.29 |
| % found | 59.54 | 6.61 | 9.95 |

EXAMPLE 55

2-[4-(1H-Indazol-1-yl)butyl]octahydro-2H-pyridol[1,2-a]pyrazine dihydrochloride

Step A: 4-(1H-Benzimidazol-1-yl)butanoic acid
The procedure is as for Example 53, Step A, using indazole as substrate.
Step B: 2-[4-(1H-Indazol-1-yl)butyl]octahydro-2H-pyrido[1,2-a]pyrazine dihydrachloride
The procedure is as for Example 53 using the compound obtained in the preceding Step A as substrate.
Melting point: 237–238° C.

Elemental microanalysis:

|  | C | H | N | Cl |
|---|---|---|---|---|
| % calculated | 59.22 | 7.85 | 14.54 | 18.40 |
| % found | 59.80 | 7.72 | 13.80 | 18.80 |

EXAMPLE 56

4-(3-Octahydro-2H-pyrido[1,2-a]pyrazin-2-ylpropoxy)benzonitrile difumarate

Step A: 4-(3-Bromopropoxy)benzonitrile
The procedure is as for Example 53, Step A, using as substrate 4-hydroxybenzonitrile and 1,3-dibromopropane.
Step B: 4-(3-Octahydro-2H-pyrido[1,2-a]pyrazin-2-ylpropoxy)benzonitrile difumarate
The procedure is as for Example 53 using the compound obtained in the preceding Step A as substrate.
Melting point: 199–200° C.

Elemental microanalysis:

|  | C | H | N |
|---|---|---|---|
| % calculated | 58.75 | 6.26 | 7.91 |
| % found | 59.19 | 6.30 | 7.85 |

EXAMPLE 57

4-(3-octahydro-2H-pyrido[1,2-a]pyrazin-2-ylpropoxy)benzonitrile difumarate, enantiomer α

EXAMPLE 58

4-(3-octahydro-2H-pyrido[1,2-a]pyrazin-2-ylpropoxy)benzonitrile difumarate, enantiomer β

The compounds o examples 57 and 58 are obtained from 0.5 g of the compound of example 56 which are separated over a CHIRALPAK AD chiral chromatography column. The fumarate is obtained in ethanol.
Enantiomer α
  Optical purity: 98.7%
  Melting point: 180–181° C.

Elemental microanalysis:

|  | C | H | N |
|---|---|---|---|
| % calculated | 58.75 | 6.26 | 7.91 |
| % found | 58.60 | 6.13 | 7.81 |

Enantiomer β
Optical purity: >99%
Melting point: 180–181° C.

Elemental microanalysis:

|  | C | H | N |
|---|---|---|---|
| % calculated | 58.75 | 6.26 | 7.91 |
| % found | 58.43 | 6.22 | 7.79 |

EXAMPLE 59

4-(4-Octahydro-2H-pyrido[1,2-a]pyrazin-2-ylbutoxy)benzonitrile difumarate

Step A: 4-(4-Bromobutoxy)benzonitrite

The procedure is as for Example 53, Step A, using as substrate 4-hydroxybenzonitrile and 1,4-dibromobutane.

Step B: 4-(4-Octahydro-2H-pyrido[1,2-a]pyrazin-2-ylbutoxy)benzonitrile difumarate The procedure is as for Example 53 using the compound obtained in the preceding Step A.

Melting point: 208–210° C.

Elemental microanalysis:

|  | C | H | N |
|---|---|---|---|
| % calculated | 59.44 | 6.47 | 7.70 |
| % found | 59.40 | 6.48 | 7.66 |

EXAMPLE 60

4-(4-octahydro-2H-pyrido[1,2-a]pyrazin-2-ylbutoxy)benzonitrile difumarate, enantiomer α

EXAMPLE 61

4-(4-octahydro-2H-pyrido[1,2-a]pyrazin-2-ylbutoxy)benzonitrile difumarate, enantiomer β

The compounds of examples 60 and 61 are obtained from 0.5 g of the compound of example 59 which are separated over a CHIRALPAK AD chiral chromatography column. The fumarate is obtained in ethanol.

Enantiomer α
Optical purity: >99%
Melting point: 208–210° C.

Elemental microanalysis:

|  | C | H | N |
|---|---|---|---|
| % calculated | 59.44 | 6.47 | 7.70 |
| % found | 59.28 | 6.36 | 7.78 |

Enantiomer β
Optical purity: >99%
Melting point: 209–210° C.

Elemental microanalysis:

|  | C | H | N |
|---|---|---|---|
| % calculated | 59.44 | 6.47 | 7.70 |
| % found | 59.28 | 6.43 | 7.75 |

EXAMPLE 62

2-[4-(2,3-dihydro-1H-indol-1-yl)butyl]octahydro-2H-pyrido[1,2-a]pyrazine trihydrochloride, enantiomer α

EXAMPLE 63

2-[4-(2,3-dihydro-1H-indol-1-yl)butyl]octahydro-2H-pyrido[1,2-a]pyrazine trihydrochloride, enantiomer β

The compounds of Examples 62 and 63 are obtained from 1 g of the compound of Example 23 which are separated over a CHIRALPAK AD chiral chromatography column. The hydrochloride is obtained by the action of an ethanolic hydrogen chloride solution.

Enantiomer α
Optical purity: >99%
Melting point: >250° C.

Elemental microanalysis:

|  | C | H | N | Cl |
|---|---|---|---|---|
| % calculated | 56.81 | 8.10 | 9.94 | 25.15 |
| % found | 57.50 | 8.10 | 9.93 | 25.17 |

Enantiomer β
Optical purity: >99%
Melting point: >250° C.

Elemental microanalysis:

|  | C | H | N | Cl |
|---|---|---|---|---|
| % calculated | 56.81 | 8.10 | 9.94 | 25.15 |
| % found | 57.29 | 8.24 | 9.89 | 25.29 |

EXAMPLE 64

4-(4-Octahydro-2H-pyrido[1,2-a]pyrazin-2-ylbutyl)-2H-1,4-benzoxazin-3(4H)-one dihydrochloride Step A: 4-(4-Bromobutyl)-2H-1,4-benzoxazin-3(4H)-one The procedure is as for Example 53, Step A, using as substrate 4H-benzo[1,4]oxazin-3-one and 1,4-dibromobutane.

Step B: 4-(4-Octahydro-2H-pyrido[1,2-a]pyrazin-2-ylbutyl)-2H-1,4-benzoxazin-3(4H)-one dihydrochloride The procedure is as for Example 53, using the compound obtained in the preceding Step A.

Melting point: >250° C.

Elemental microanalysis:

|  | C | H | N | Cl |
|---|---|---|---|---|
| % calculated | 57.69 | 7.50 | 10.09 | 17.03 |
| % found | 57.59 | 7.85 | 10.01 | 17.43 |

EXAMPLE 65

4-(4-Octahydro-2H-pyrido[1,2-a]pyrazin-2-ylbutyl)-3,4-dihydro-2H-1,4-benzoxazine trihydrochloride The procedure is as for Example 16 using the compound obtained in Example 64 as substrate.

Melting point: 203–205° C.

Elemental microanalysis:

|  | C | H | N | Cl |
|---|---|---|---|---|
| % calculated | 54.74 | 7.81 | 9.57 | 24.23 |
| % found | 54.56 | 7.94 | 9.34 | 23.63 |

EXAMPLE 66

2-(4-Octahydro-2H-pyrido[1,2-a]pyrazin-2-ylbutoxy)benzonitrile difumarate

Step A: 2-(-4-Bromobutoxy)benzonitrile

The procedure is as for Example 53, Step A, using as substrate 2-hydroxybenzonitrile and 1,4-dibromobutane.

Step B: 2-(4-Octahydro-2H-pyrido[1,2-a]pyrazin-2-ylbutoxy)benzonitrile difumarate The procedure is as for Example 53 using the compound obtained in the preceding Step A.

Melting point: 154–155° C.

Elemental microanalysis:

|  | C | H | N |
|---|---|---|---|
| % calculated | 59.44 | 6.47 | 7.70 |
| % found | 56.14 | 6.41 | 7.74 |

EXAMPLE 67

3-(4-Octahydro-2H-pyrido[1,2-a]pyrazin-2-ylbutoxy)benzonitrile difumarate

Step A: 3-(4-Bromobutoxy)benzonitrile

The procedure is as for Example 53, Step A, using as substrate 3-hydroxybenzonitrile and 1,4-dibromobutane.

Step B: 3-(4-Octahydro-2H-pyrido[1,2-a]pyrazin-2-ylbutoxy)benzonitrile difumarate The procedure is as for Example 53 using the compound obtained in the preceding Step A.

Melting point: 167–168° C.

Elemental microanalysis:

|  | C | H | N |
|---|---|---|---|
| % calculated | 59.44 | 6.47 | 7.70 |
| % found | 59.33 | 6.36 | 7.92 |

EXAMPLE 68

4-(2-Octahydro-2H-pyrido[1,2-a]pyrazin-2-ylethoxy)benzonitrile difumarate

Step A: 4-(2-Bromoethoxy)benzonitrile

The procedure is as for Example 53, Step A, using as substrate 4-hydroxybenzonitrile and 1,2-dibromoethane.

Step B  4-(2-Octahydro-2H-pyrido[1,2-a]pyrazin-2-ylethoxy)benzonitrile difumarate The procedure is as for Example 53 using the compound obtained in the preceding Step A.

Melting point: 159–160° C.

Elemental microanalysis:

|  | C | H | N |
|---|---|---|---|
| % calculated | 58.02 | 6.04 | 8.12 |
| % found | 57.98 | 5.87 | 8.13 |

EXAMPLE 69

3-Methoxy-4-(4-octahydro-2H-pyrido[1,2-a]pyrazin-2-ylbutoxy)benzonitrile difumarate Step A: 4-(4-Bromobutoxy)-3-methoxybenzonitrile The procedure is as for Example 53, Step A, using as substrate 4-hydroxy-3-methoxybenzonitrile and 1,4-dibromobutane.

Step B: 3-Methoxy-4-(4-octahydro-2H-pyrido[1,2-a]pyrazin-2-ylbutoxy)benzonitrile difumarate The procedure is as for Example 53 using the compound obtained in the preceding Step A.

Melting point: 195–196° C.

Elemental microanalysis:

|  | C | H | N |
|---|---|---|---|
| % calculated | 58.43 | 6.48 | 7.30 |
| % found | 58.30 | 6.30 | 7.48 |

EXAMPLE 70

2-[3-(1H-Indol-1-yl)propyl]octahydro-2H-pyrido[1,2-a]pyrazine dihydrochloride Step A: 1-(3-Bromopropyl)-1H-benzimidazole The procedure is as for Example 53, Step A, using as substrate indole and 1,3-dibromopropane.

Step B: 2-[3-(1H-Indol-1-yl)propyl]octahydro-2H-pyrido[ ],2-a]pyrazine dihydrochloride The procedure is as for Example 53 using the compound obtained in the preceding Step A.

Melting point: 246–247° C.

| Elemental microanalysis: | | | | |
|---|---|---|---|---|
| | C | H | N | Cl |
| % calculated | 61.62 | 7.89 | 11.35 | 19.14 |
| % found | 61.25 | 7.87 | 11.25 | 19.20 |

EXAMPLE 71

2-[4-(2,3,4-Trimethoxyphenoxy)butyl]octahydro-2H-pyrido[1,2-a]pyrazine dihydrochloride Step A: 1-(4-Bromobutoxy)-2,3,4-trimethoxybenzene The procedure is as for Example 53, Step A, using as substrate 2,3,4-trimethoxyphenol and 1,4-dibromobutane.

Step B: 2-[4-(2,3,4-Trimethoxyphenoxy)butyl]octahydro-2H-pyrido[1,2-a]pyrazine dihydrochloride The procedure is as for Example 53 using the compound obtained in the preceding Step A.

Melting point: 211–212° C.

| Elemental microanalysis: | | | | |
|---|---|---|---|---|
| | C | H | N | Cl |
| % calculated | 55.87 | 8.04 | 6.21 | 15.71 |
| % found | 55.43 | 7.87 | 6.26 | 16.17 |

EXAMPLE 72

2-Methoxy-4-(4-octahydro-2H-pyrido[1,2-a]pyrazin-2-ylbutoxy)benzonitrile difumarate Step A: 4-(4-Bromobutoxy)-2-methoxybenzonitrile The procedure is as for Example 53, Step A, using as substrate 4-hydroxy-2-methoxy-benzonitrile and 1,4-dibromobutane.

Step B: 2-Methoxy-4-(4-octahydro-2H-pyrido[1,2-a]pyrazin-2-yl-butoxy)benzonitrile difumarate The procedure is as for Example 53 using the compound obtained in the preceding Step A.

Melting point: 164–165° C.

| Elemental microanalysis: | | | |
|---|---|---|---|
| | C | H | N |
| % calculated | 64.42 | 4.73 | 9.39 |
| % found | 64.27 | 4.64 | 9.46 |

EXAMPLE 73

2-[4-(1H-indol-1-yl)butyl]octahydro-2H-pyrido[1,2-a]pyrazine dihydrochloride, enantiomer α

EXAMPLE 74

2-[4-(1H-indol-1-yl)butyl]octahydro-2H-pyrido[1,2-a]pyrazine dihydrochloride, enantiomer β

The compounds of Examples 73 and 74 are obtained from 1 g of the compound of Example 39 which are separated over a CHIRALPAK AD chiral chromatography column. The hydrochloride is obtained in ethanol.

Enantiomer α
Optical purity: >99%

Enantiomer β
Optical purity: >98%

EXAMPLE 75

1-(4-Octahydro-2H-pyrido[1,2-a]pyrazin-2-ylbutyl)-1H-indole-5-carbonitrile difumarate Step A: 1-(4-Bromobutyl)-1H-indole-5-carbonitrile The procedure is as for Example 39 using as substrate 1H-indole-5-carbonitrile and 1,4-dibromobutane.

Step B: 1-(4-Octahydro-2H-pyridol[1,2-a]pyrazin-2-ylbutyl)-1H-indole-5-carboiitrile difumarate The procedure is as for Example 39 using the compound obtained in the preceding Step A as substrate.

EXAMPLE 76

2-[4-(5-Metboxy-1H-indol-1-yl)butyl]octahydro-2H-pyrido[1,2-a]pyrazine dihydrochloride Step A: 1-(4-Bromobutyl)-5-methoxy-1H-indole The procedure is as for Example 39 using as substrate 5-methoxy-1H-indole and 1,4-dibromobutane.

Step B 2-[4-(5-Methoxy-1H-indol-1-yl)butyl]octahydro-2H-pyrido[1,2-a]pyrazine dihydrochloride The procedure is as for Example 39 using the compound obtained in the preceding Step A as substrate.

EXAMPLE 77

2-[2-(1H-Indol-1-yl)ethyl]octahydro-2H-pyrido[1,2-a]pyrazine dihydrochloride Step A: 1-(2-Bromoethyl)-1H-indole The procedure is as for Example 39 using as substrate 1H-indole and 1,2-dibromoethane.

Step B: 2-[2-(1H-Indol-1-yl)ethyl]octahydro-2H-pyrido[1,2-a]pyrazine dihydrochloride The procedure is as for Example 39 using the compound obtained in the preceding Step A as substrate.

EXAMPLE 78

2-[4-(4-Bromophenoxy)butyl]octahydro-2H-pyridol[1,2-a]pyrazine dihydrochloride

Step A: 1-Bromo-4-(4-bromobutoxy)benzene

The procedure is as for Example 53 using as substrate 4-bromophenol and 1,4-dibromobutane.

Step B: 2-[4-(4-Bromophenoxy)butyl]octahydro-2H-pyrido[1,2-a]pyrazine dihydrochloride The procedure is as for Example 53 using the compound obtained in the preceding Step A as substrate.

EXAMPLE 79

1-[4-(4-Octahydro-2H-pyridol[1,2-a]pyrazin-2ylbutoxy)phenyl]ethanone difumarate

Step A: 2-{4-[4-(Tributylstannyl)phenoxy]butyl}octahydro-2H-pyrido[1,2-a]pyrazine 5 g of the compound obtained in Example 78 are refluxed under an inert atmosphere for 2 hours in the presence of 10 ml of hexabutyl distannane, 0.5 g of tetrakis-triphenylphosphinepalladium and 100 ml of toluene. The expected product is obtained by removal of the solvent by evaporation and purification over a silica column (eluant:CH$_2$Cl$_2$/MeOH, 95/5).

Step B: 1-[4-(4-Octahydro-2H-pyrido[1,2-a]pyrazin-2-yl-butoxyphenyl]ethanone difumarate 0.6 g of the compound obtained in Step A, 85 μl of acetyl chloride, 8 mg of Pd$_2$dba$_3$ and 50 ml of toluene are refluxed for 1 hour under an inert atmosphere. The solvent is then removed by evaporation and the residue is purified over a silica column (eluant:CH$_2$Cl$_2$/MeOH, 95/5) to yield the expected product, which is converted to the fumarate in a mixture of ethanol/ether.

EXAMPLE 80

Cyclopropyl[4-(4-octahydro-2H-pyrido[1,2-a]pyrazin-2-ylbutoxy)phenyl]methanone difumarate The procedure is as for Example 79, Step B using the compound obtained in Step A of Example 79 and cyclopropylcarboxylic acid chloride.

EXAMPLE 81

Cyclohexyl[4-(4-octahydro-2H-pyrido[1,2-a]pyrazin-2-ylbutoxy)-phenyl]methanone difumarate The procedure is as for Example 79, Step B using the compound obtained in Step A of Example 79 and cyclohexanecarboxylic acid chloride.

EXAMPLE 82

2-Methyl-1-[4-(4-octahydro-2H-pyrido[1,2-a]pyrazin-2-ylbutoxy)-phenyl]-1-propanone difumarate The procedure is as for Example 79, Step B, using the compound obtained in Step A of Example 79 and 2-methylpropanoic acid chloride.

EXAMPLE 83

[4-(4-Octahydro-2H-pyrido[1,2-a]pyrazin-2-ylbutoxy)-phenyl](phenyl)methanone difumarate The procedure is as for Example 79, Step B using the compound obtained in Step A of Example 79 and benzoic acid chloride.

EXAMPLE 84

(1E)-1-[4-(4-Octahydro-2H-pyrido[1,2-a]pyrazin-2-ylbutoxy)phenyl]ethanone oxime difumarate 0.33 g of the compound obtained in Example 79, 0.070 g of hydroxylamine hydrochloride and 0.14 g of potassium carbonate are refluxed in 20 ml of ethanol for 1 hour. The solvent is then evaporated to dryness and the residue is chromatographed over a silica column (CH$_2$Cl$_2$/MeOH, 95/5). The expected product is converted to the fumarate in a mixture of ethanol/ether.

EXAMPLE 85

2-[4-(4-Ethynylphenoxy)butyl]octahydro-2H-pyrido[1,2-a]pyrazine dihydrochloride 370 mg of the compound obtained in Example 78, 10 ml of triethylamine, 190 mg of copper (I) iodide, 0.28 ml of trimethylsilyl acetylene and 10 mg of tetrakisphenylphosphine are heated at 60° C. for 1 hour. The reaction mixture is then evaporated to dryness and taken up in 2 ml of a 1M solution of TBAF in THF and 10 ml of dichloromethane. After purification by chromatography over silica (eluant: CH$_2$Cl$_2$/MeOH, 95/5), the residue is converted to the hydrochloride using an ethanolic hydrogen chloride solution.

The following Examples were prepared by purification by chromatography over a silica column and by chiral chromatography using the corresponding starting materials.

EXAMPLE 86

4-[(4-Octahydro-2H-pyrido[1,2-a]pyrazin-2-ylpentyl)oxy]benzonitrile difumarate, pair A EXAMPLE 86a 4-[(4-Octahydro-2H-pyrido[1,2-a]pyrazin-2-ylpentyl)oxy]benzonitrile difumarate, enantiomer α

EXAMPLE 86b

4-[(4-Octahydro-2H-pyrido[1,2-a]pyrazin-2-ylpentyl)oxy]benzonitrile difumarate, enantiomer β

EXAMPLE 87

4-[(4-Octahydro-2H-pyrido[1,2-a]pyrazin-2-ylpentyl)oxy]benzonitrile difumarate, pair B

EXAMPLE 87a

4-[(4-Octahydro-2H-pyrido[1,2-a]pyrazin-2-ylpentyl)oxy]benzonitrile difumarate, enantiomer γ

EXAMPLE 87b

4-[(4-Octahydro-2H-pyrido[1,2-a]pyrazin-2-ylpentyl)oxy]benzonitrile difumarate, enantiomer δ

EXAMPLE 88

4-(1-Methyl-4-octahydro-2H-pyrido[1,2-a]pyrazin-2-ylbutoxy)benzonitrile difumarate, pair A

EXAMPLE 88a 4-(1-Methyl-4-octahydro-2H-pyrido[1,2-a]pyrazin-2-ylbutoxy)benzonitrile difumarate, enantiomer α

EXAMPLE 88b 4-(1-Methyl-4-octahydro-2H-pyrido[1,2-a]pyrazin-2-ylbutoxy)benzonitrile difumarate, enantiomer β

EXAMPLE 89

4-(1-Methyl-4-octahydro-2H-pyrido[1,2-a]pyrazin-2-ylbutoxy)benzonitrile difumarate, pair B

EXAMPLE 89a 4-(1-Methyl-4-octahydro-2H-pyrido[1,2-a]pyrazin-2-ylbutoxy)benzonitrile difumarate, enantiomer γ

EXAMPLE 89b 4-(1-Methyl-4-octahydro-2H-pyrido[1,2-a]pyrazin-2-ylbutoxy)benzonitrile difumarate, enantiomer δ

EXAMPLE 90

4-(2-Methyl-4-octahydro-2H-pyrido[1,2-a]pyrazin-2-ylbutoxy)benzonitrile difumarate, pair A

EXAMPLE 90a 4-(2-Methyl-4-octahydro-2H-pyrido[1,2-a]pyrazin-2-ylbutoxy)benzonitrile difumarate, enantiomer α

EXAMPLE 90b 4-(2-Methyl-4-octahydro-2H-pyrido[1,2-a]pyrazin-2-ylbutoxy)benzonitrile difumarate, enantiomer β

EXAMPLE 91

4-(2-Methyl-4-octahydro-2H-pyrido[1,2-a]pyrazin-2-ylbutoxy)benzonitrile difumarate, pair B

EXAMPLE 91a 4-(2-Methyl-4-octahydro-2H-pyrido[1,2-a]pyrazin-2-ylbutoxy)benzonitrile difumarate, enantiomer γ

EXAMPLE 91b 4-(2-Methyl-4-octahydro-2H-pyrido[1,2-a]pyrazin-2-ylbutoxy)benzonitrile difumarate, enantiomer δ

EXAMPLE 92

4-(3-Methyl-4-octahydro-2H-pyrido[1,2-a]pyrazin-2-ylbutoxy)benzonitrile difumarate, pair A

EXAMPLE 92a 4-(3-Methyl-4-octahydro-2H-pyrido[1,2-a]pyrazin-2-ylbutoxy)benzonitrile difumarate, enantiomer α

EXAMPLE 92b 4-(3-Methyl-4-octahydro-2H-pyrido[1,2-a]pyrazin-2-ylbutoxy)benzonitrile difumarate, enantiomer β

EXAMPLE 93

4-(3-Methyl-4-octahydro-2H-pyrido[1,2-a]pyrazin-2-ylbutoxy)benzonitrile difumarate, pair B

EXAMPLE 93a 4-(3-Methyl-4-octahydro-2H-pyrido[1,2-a]pyrazin-2-ylbutoxy)benzonitrile difumarate, enantiomer γ

EXAMPLE 93b 4-(3-Methyl-4-octahydro-2H-pyrido[1,2-a]pyrazin-2-ylbutoxy)benzonitrile difumarate, enantiomer δ

EXAMPLE 94

2-[4-(5-Bromo-1H-indol-1-yl)butyl]octahydro-2H-pyrido[1,2-a]pyrazine difumarate

Step A: 4-Bromo-1-(4-bromobutyl)-1H-indole
The procedure is as for Example 39 using as substrate 5-bromo-1H-indole and 1,4-dibromobutane.

Step B: 2-[4-(5-Bromo-1H-indol-1-yl)butyl]octahydro-2H-pyrido]1,2-a]pyrazine difumarate The procedure is as for Example 39 using the compound obtained in the preceding Step A as substrate.

EXAMPLE 95

2-{4-[5-(Trifluoromethyl)-1H-indol-1-yl]butyl}octahydro-2H-pyrido[1,2-a]pyrazine difumarate Step A: 1-(4-Bromobutyl)-4-(trifluoromethyl)-1H-indole The procedure is as for Example 39 using as substrate 5-trifluoromethyl-1H-indole, which is prepared according to the procedure described in Heterocycles, 57, 2, 2002, p. 465, and 1,4-dibromobutane.

Step B. 2-{4-[5-(Trifloromethyl)-1H-indol-1-yl]butyl}octahydro-2H-pyrido-[1,2-a]pyrazine difumarate The procedure is as for Example 39 using the compound obtained in the preceding Step A as substrate.

EXAMPLE 96

2-[4-(4,6-Dichloro-1H-indol-1-yl)butyl]octahydro-2H-pyrido-[1,2-a]pyrazine difumarate Step A: 1-(4-Bromobutyl)-4,6-diciloro-1H-indole The procedure is as for Example 39 using as substrate 4,6-dichloro-1H-indole and 1,4-dibromobutane.

Step B: 2-[4-(4,6-Dichloro-1H-indol-1-yl)butyl]octahydro-2H-pyrido-[1,2-a]pyrazine difumarate The procedure is as for Example 39 using the compound obtained in the preceding Step A as substrate.

EXAMPLE 97

2-[4-(5,7-Dichloro-1H-indol-1-yl)butyl]octahydro-2H-pyrido-[1,2-a]pyrazine difumarate Step A: 1-(4-Bromobutyl)-5,7-dichloro-1H-indole The procedure is as for Example 39 using as substrate 5,7-dichloro-1H-indole and 1,4-dibromobutane.

Step B: 2-[4-(5,7-Dichloro-1H-indol-1-yl)butyl]octahydro-2H-pyrido-[1,2-a]pyrazine difumarate The procedure is as for Example 39 using the compound obtained in the preceding Step A as substrate.

Pharmacological Studies of the Compounds of the Invention

EXAMPLE 98

Cerebral Dosages of $N^r$-methylhistamine in the NMRI Mouse

The purpose of this study, which was carried out in accordance with the method of Taylor et al. (Biochem. Pharm., 1992, 44, 1261–1267), is to evaluate the ex vivo activity of the compounds of the present invention as antagonists of type H3 central histamine receptors. That activity is revealed by measuring, after treatment intraperitoneally with the test compounds, the central levels of $N^r$-methylhistamine, which is a main metabolite of histamine. An increase in the cerebral concentrations of $N^r$-methylhistamine indicates an increase in the turn-over of histamine by blockage of the type H3 central histamine receptors.

NMRI mice (18–20 g) are treated intraperitoneally with compounds of the present invention or with their carrier (20 ml/kg). One hour after the pharmacological treatment, the animals are sacrificed, and their brains are removed, frozen in liquid nitrogen, weighed and homogenised in 0.1N $HClO_4$ at 4° C. The homogenised products are centrifuged (15000 g, 17 min, 4° C.). The supernatants are recovered and divided into aliquots. The aliquots are frozen in liquid nitrogen and stored at −80° C. until analysis.

Determination of the cerebral levels of $N^r$-methylhistamine is carried out by radioimmunological assay (RIA) using an assay kit. The tissue levels of $N^r$-methylhistamine are expressed in μg/g of fresh brain. The comparison of the cerebral levels of $N^r$-methylhistamine between animals treated with the carrier (controls) and animals treated with compounds of the present invention is carried out by single factor variance analysis followed, if necessary, by a complementary analysis (Dunnett test).

The results show that, at doses of from 3 to 30 mg/kg IP, the compounds of the present invention are capable of increasing endogenous cerebral concentrations of $N^r$-methyl-histamine by 50%. By way of illustration, the compounds of Examples 53 and 55, at dose of 30 mg/kg IP, increase endogenous cerebral concentrations of $N^r$-methyl-histamine by 89% and 124%, respectively and, the compounds of Examples 56 and 58, at doses of 10 mg/kg IP, increase endogenous cerebral concentrations of $N^r$-methyl-histamine by 252% and 236%, respectively. Those results demonstrate that the compounds of the present invention are powerful antagonists of type H3 central histamine receptors.

EXAMPLE 99

Pharmaceutical Compositions

Formulation for the preparation of 1000 tablets containing a dose of 100 mg of active ingredient:

| | |
|---|---|
| Compound of Example 1 | 100 g |
| Hydroxypropylcellulose | 20 g |
| Polyvinylpyrrolidone | 20 g |
| Wheat starch | 150 g |
| Lactose | 900 g |
| Magnesium stearate | 30 g |

What is claimed is:

1. A compound selected from those of formula (I):

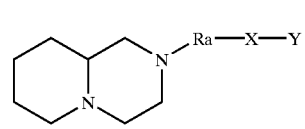

wherein:
Ra represents linear or branched ($C_1$–$C_6$)alkylene,
Y represents aryl,
X represents a group selected from $W_1$, —C($W_1$)—$W_2$—, —$W_2$—C($W_1$)—, —$W_2$—C($W_1$)$W_2$—, and —$W_2$—Ra—, wherein $R_a$ has the same meaning as $R_a$, and wherein:
$W_1$ represents oxygen, sulphur, or a group of formula —$NR_2$ wherein $R_2$ represents hydrogen, linear or branched ($C_1$–$C_6$)-alkyl, aryl, aryl-($C_1$–$C_6$)alkyl in which the alkyl moiety is linear or branched, and linear or branched ($C_1$–$C_6$)acyl, and $W_2$ represents a group as defined for $W_1$, or X represents —CH(OR$_1$) wherein $R_1$ is selected from hydrogen or linear or branched ($C_1$–$C_6$)alkyl, provided that —$W_2$—C($W_1$)— is not O—C(O)—, its enantiomers, diastereoisomers, and addition salts thereof with a pharmaceutically acceptable acid or base, with the proviso that the compound may not be:

2-octahydro-2H-pyrido[1,2-a]pyrazin-2-yl-1-phenylethanol, 3-octahydro-2H-pyrido[1,2-a]pyrazin-2-ylpropyl-3,4,5-trimethoxybenzoate, and 2-octahydro-2H-pyrido[1,2-a]pyrazin-2-ylethyl-3,4,5-trimethoxybenzoate, it also being understood that:

"aryl group" is a monocyclic or bicyclic aromatic system, having from 5 to 10 carbon atoms, optionally substituted by one or more identical or different groups each independently of the others selected from halogen, nitro, cyano, hydroxy, linear or branched ($C_1$–$C_6$) alkoxy, aryloxy, aryl-($C_1$–$C_6$)-alkoxy in which the alkoxy moiety is linear or branched, linear or branched ($C_1$–$C_6$)alkyl, linear or branched ($C_2$–$C_6$)alkenyl, linear or branched ($C_2$–$C_6$)alkynyl, linear or branched trihalo-($C_1$–$C_6$)alkyl, carboxy, linear or branched ($C_1$–$C_6$)alkoxy-carbonyl, linear or branched ($C_1$–$C_6$) acyl, linear or branched ($C_1$–$C_6$)acyloxy, —SH, linear or branched ($C_1$–$C_6$)alkylthio, methylenedioxy, ethylenedioxy, —C(CH$_3$)=N—OH, and amino optionally substituted by one or two identical or different groups each independently of the other selected from linear or branched ($C_1$–$C_6$)alkyl, aryl, aryl-($C_1$–$C_6$)alkyl in which the alkyl moiety is linear or branched, and linear or branched ($C_1$–$C_6$)acyl.

2. A compound of claim 1, wherein Ra represents linear ($C_2$–$C_5$)alkylene.

3. A compound of claim 1, wherein $R_2$ represents hydrogen, linear or branched ($C_1$–$C_6$)alkyl, or linear or branched ($C_1$–$C_6$)-acyl.

4. A compound of claim 1, wherein X represents a group selected from oxygen and groups —C($W_1$)—$W_2$—, —$W_2$—C($W_1$)— and —N($R_2$)— wherein $W_1$ represents oxygen, $W_2$ represents oxygen or a group —N$R_2$ and $R_2$ represents hydrogen, linear or branched ($C_1$–$C_6$)alkyl, aryl, aryl-($C_1$–$C_6$)alkyl in which the alkyl moiety is linear or branched, and linear or branched ($C_1$–$C_6$)acyl.

5. A compound of claim 1, wherein $Y_1$ represents phenyl optionally substituted by from 1 to 3 halogen, cyano, hydroxy, linear or branched ($C_1$–$C_6$)alkoxy, aryloxy, aryl-($C_1$–$C_6$)alkoxy in which the alkoxy moiety is linear or branched, linear or branched ($C_1$–$C_6$)alkyl, linear or branched trihalo-($C_1$–$C_6$)-alkyl, methylenedioxy and ethylenedioxy.

6. A compound of claim 1 which is selected from:

2-[4-(3,4,5-trimethoxyphenoxy)butyl]octahydro-2H-pyrido[1,2-a]pyrazine,

2-[4-(3,4,5-trimethoxyphenoxy)butyl]octahydro-2H-pyrido[1,2-a]pyrazine, enantiomer α, 2-[4-(3,4,5-trimethoxyphenoxy)butyl]octahydro-2H-pyrido[1,2-a]pyrazine, enantiomer β, N-(4-octahydro-2H-pyrido[1,2-a]pyrazin-2-ylbutyl)-N-(3,4,5-trimethoxyphenyl)amine, N-(4-octahydro-2H-pyrido[1,2-a]pyrazin-2-ylbutyl)-N-(3,4,5-trimethoxyphenyl)-amine, enantiomer α, N-(4-octahydro-2H-pyrido[1,2-a]pyrazin-2-ylbutyl)-N-(3,4,5-trimethoxyphenyl)-amine, enantiomer β, N-(4-trifluorophenyl)-N-(4-octahydro-2H-pyrido[1,2-a]pyrazin-2-ylbutyl)amine trihydrochloride, N-(3,4-dichloro-phenyl)-N-(4-octahydro-2H-pyrido[1,2-a]pyrazin-2-ylbutyl)amine, N-(3,5-dichloro-phenyl)-N-(4-octahydro-2H-pyrido[1,2-a]pyrazin-2-ylbutyl)amine, N-(2-chlorophenyl)-N-(4-octahydro-2H-pyrido[1,2-a]pyrazin-2-ylbutyl)amine, 3-(4-octahydro-2H-pyrido[1,2-a]pyrazin-2-ylbutoxy)benzonitrile, 3-methoxy-4-(4-octahydro-2H-pyrido[1,2-a]pyrazin-2-ylbutoxy)benzonitrile, 2-[4-(2,3,4-trimethoxyphenoxy)butyl]octahydro-2H-pyrido[1,2-a]pyrazine, its enantiomers, diastereoisomers, and addition salts thereof with a pharmaceutically acceptable acid or base.

7. A compound of claim 1 which is selected from:

4-[(4-octahydro-2H-pyrido[1,2-a]pyrazin-2-ylbutyl)amino]benzonitrile,

4-[(3-octahydro-2H-pyrido[1,2-a]pyrazin-2-ylpropoxy)benzonitrile,

4-[(3-octahydro-2H-pyrido[1,2-a]pyrazin-2-ylpropoxy)benzonitrile, enantiomer α,

4-[(3-octahydro-2H-pyrido[1,2-a]pyrazin-2-ylpropoxy)benzonitrile, enantiomer β, 4-(4-octahydro-2H-pyrido[1,2-a]pyrazin-2-ylbutoxy)benzonitrile, 4-(4-octahydro-2H-pyrido[1,2-a]pyrazin-2-ylbutoxy)benzonitrile, enantiomer α, 4-(4-octahydro-2H-pyrido[1,2-a]pyrazin-2-ylbutoxy)benzonitrile, enantiomer β, 4-(2-octahydro-2H-pyrido[1,2-a]pyrazin-2-ylethoxy)benzonitrile, its enantiomers, diastereoisomers, and addition salts thereof with a pharmaceutically acceptable acid or base.

8. A pharmaceutical composition comprising as active principle an effective amount of a compound as claimed in claim 1, together with one or more pharmaceutical acceptable excipients or vehicles.

9. A method for treating a living animal body afflicted with a disease requiring an antagonist of type $H_3$ central histamine receptors, selected from cognitive deficiencies associated with Alzheimer's disease, Parkinson's disease, and/or schizophrenia; mood disorders; convulsive attacks; and obesity, comprising the step of administering to the living body an amount of a compound of claim 1 which is effective for alleviation of the condition.

10. A method for treating a living animal body afflicted with cognitive deficiencies associated with Alzheimer's disease and/or Parkinson's disease, comprising the step of administering to the living body an amount of a compound of claim 1 which is effective for alleviation of the deficiency.

* * * * *

UNITED STATES PATENT AND TRADEMARK OFFICE
CERTIFICATE OF CORRECTION

PATENT NO. : 6,992,085 B2
DATED : January 31, 2006
INVENTOR(S) : Solo Goldstein et al.

It is certified that error appears in the above-identified patent and that said Letters Patent is hereby corrected as shown below:

Column 50,
Line 8, "trihydrochioride" should be -- trihydrochloride --.

Signed and Sealed this

Twenty-third Day of May, 2006

JON W. DUDAS
*Director of the United States Patent and Trademark Office*